US012774328B2

(12) United States Patent
Soon-Shiong et al.

(10) Patent No.: US 12,774,328 B2
(45) Date of Patent: *Oct. 27, 2026

(54) METHODS OF REDUCING EPITHELIAL-MESENCHYMAL TRANSITION WITH AN INTERLEUKIN-8 ANTIBODY

(71) Applicant: NantBio, Inc., Culver City, CA (US)

(72) Inventors: Patrick Soon-Shiong, Culver City, CA (US); Kayvan Niazi, Culver City, CA (US); Shiho Tanaka, Culver City, CA (US); Jon Thomas Van Lew, Culver City, CA (US); Clifford Anders Olson, Culver City, CA (US); Philip T. Liu, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 731 days.

This patent is subject to a terminal disclaimer.

(21) Appl. No.: 18/325,860

(22) Filed: May 30, 2023

(65) Prior Publication Data

US 2023/0406918 A1 Dec. 21, 2023

Related U.S. Application Data

(60) Continuation of application No. 16/928,530, filed on Jul. 14, 2020, now Pat. No. 11,773,158, which is a division of application No. 16/174,040, filed on Oct. 29, 2018, now Pat. No. 10,752,682.

(60) Provisional application No. 62/580,232, filed on Nov. 1, 2017.

(51) Int. Cl.

| | |
|---|---|
| ***C07K 16/24*** | (2006.01) |
| ***A61K 38/17*** | (2006.01) |
| ***A61K 38/20*** | (2006.01) |
| ***A61K 39/00*** | (2006.01) |
| ***A61K 39/395*** | (2006.01) |
| ***A61K 45/06*** | (2006.01) |
| ***A61P 35/00*** | (2006.01) |
| ***C07K 14/54*** | (2006.01) |
| ***C07K 14/715*** | (2006.01) |

(52) U.S. Cl.

CPC ........ *C07K 16/244* (2013.01); *A61K 38/1793* (2013.01); *A61K 38/2086* (2013.01); *A61K 39/3955* (2013.01); *A61K 45/06* (2013.01); *A61P 35/00* (2018.01); *A61K 2039/545* (2013.01); *C07K 14/5443* (2013.01); *C07K 14/7155* (2013.01); *C07K 2317/21* (2013.01); *C07K 2317/24* (2013.01); *C07K 2317/33* (2013.01); *C07K 2317/35* (2013.01); *C07K 2317/56* (2013.01); *C07K 2317/565* (2013.01); *C07K 2317/622* (2013.01); *C07K 2317/76* (2013.01); *C07K 2317/92* (2013.01); *C07K 2319/30* (2013.01)

(58) Field of Classification Search

CPC .............. C07K 16/244; A61K 38/1793; A61K 38/2086; A61K 39/3955; A61P 35/00

See application file for complete search history.

(56) References Cited

U.S. PATENT DOCUMENTS

| | | | |
|---|---|---|---|
| 5,849,903 | A | 12/1998 | Pietrzkowski et al. |
| 6,117,980 | A | 9/2000 | Gonzalez et al. |
| 6,133,426 | A | 10/2000 | Gonzalez et al. |
| 7,189,820 | B2 | 3/2007 | Ruben |
| 8,105,588 | B2 | 1/2012 | Teeling et al. |
| 8,383,115 | B2 | 2/2013 | Kaushik et al. |
| 8,604,174 | B2 | 12/2013 | Babcook et al. |
| 10,752,682 | B2 | 8/2020 | Soon-Shiong et al. |
| 2003/0068319 | A1 | 4/2003 | Bar-Eli |
| 2005/0142136 | A1 | 6/2005 | Suva et al. |
| 2009/0208491 | A1 | 8/2009 | Gurney et al. |
| 2011/0052577 | A1 | 3/2011 | Kingsman et al. |

(Continued)

FOREIGN PATENT DOCUMENTS

| | | | |
|---|---|---|---|
| CA | 2 790 013 | A1 | 9/2011 |
| CA | 3 080 429 | A1 | 5/2019 |

(Continued)

OTHER PUBLICATIONS

Serrano-Gomez et al. Regulation of epithelial-mesenchymal transition through epigenetic and posttranslational modifications. Molecular Cancer. 15:18. 2016, DOI 10.1186/s12943-016-0502-x. (Year: 2016).*

David et al. The IL-8/IL-8R axis: a double agent in tumor immune resistance. Vaccines. 4, 22; 2016, doi: 10.3390/vaccines4030022. (Year: 2016).*

Palena et al. "Influence of IL-8 on the epithelial-mesenchymal transition and the tumor microenvironment" Future Oncol., Apr. 2012, vol. 8, No. 6, pp. 713-722.

Fernando et al. "IL-8 signaling plays a critical role in the epithelial-mesenchymal transition of human carcinoma cells" Cancer Research, Aug. 2011, vol. 71, No. 15, 12 pages.

(Continued)

*Primary Examiner* — Elly-Gerald Stoica

(74) *Attorney, Agent, or Firm* — Zipser LLP; Martin Fessenmaier; Priti Phukan

(57) ABSTRACT

Compositions, methods, and uses of recombinant IL-8 antibody, fragment thereof or single chain variable fragment (scFv) having high affinity to IL-8 to target tumor-expressed or endogenous IL-8 are presented. Preferably, the recombinant IL-8 antibody or scFv fragment includes a $V_H$ segment comprising a first amino acid sequence selected from SEQ ID NO. 1-15, 31-32, and/or a $V_L$ segment comprising a second amino acid sequence selected from SEQ ID NO. 16-30, 33-34. The recombinant IL-8 antibody or scFv fragment can be formulated as pharmaceutical compositions to administer to a patient having a tumor to reduce metastasis of the tumor, reduce immune suppression in the tumor microenvironment or reduce Th2 mediated immune response.

20 Claims, 10 Drawing Sheets

Specification includes a Sequence Listing.

(56) References Cited

U.S. PATENT DOCUMENTS

| | | | |
|---|---|---|---|
| 2012/0059670 A1 | 3/2012 | Sanborn et al. |
| 2012/0066001 A1 | 3/2012 | Sanborn et al. |
| 2014/0170156 A1 | 6/2014 | Teeling et al. |
| 2019/0127458 A1 | 5/2019 | Soon-Shiong et al. |

FOREIGN PATENT DOCUMENTS

| | | | |
|---|---|---|---|
| CN | 1297480 | A | 5/2001 |
| CN | 1660912 | A | 8/2005 |
| CN | 101343323 | A | 1/2009 |
| CN | 101348526 | A | 1/2009 |
| CN | 102199209 | A | 9/2011 |
| CN | 102199210 | A | 9/2011 |
| CN | 103656676 | A | 3/2014 |
| CN | 111615518 | A | 9/2020 |
| EP | 0 770 628 | A1 | 5/1997 |
| EP | 1 415 998 | A2 | 5/2004 |
| JP | H10-182486 | A | 7/1998 |
| JP | 2006-523088 | A | 10/2006 |
| JP | 2008-536517 | A | 9/2008 |
| JP | 2021-500913 | A | 1/2021 |
| KR | 10-2020-0068746 | A | 6/2020 |
| TW | 2019/22772 | A | 6/2019 |
| WO | 02/00729 | A2 | 1/2002 |
| WO | 2004058797 | A2 | 7/2004 |
| WO | 2006/113643 | A2 | 10/2006 |
| WO | 2017/156178 | A1 | 9/2017 |
| WO | 2018/005973 | A1 | 1/2018 |
| WO | 2019/089472 | A1 | 5/2019 |
| WO | 2019/067951 | A3 | 7/2019 |

OTHER PUBLICATIONS

Zhou et al. "IL-8 induces the epithelial-mesenchymal transition of renal cell carcinoma cells through the activation of AKT signaling", Oncology Letters 12, 2016, pp. 1915-1920.
Ding et al. "Generation of High-Affinity Fully Human Anti-Interleukin-8 Antibodies from its cDNA by Two-Hybrid Screening and Affinity Maturation in Yeast" Protein Science 2010, vol. 19 pp. 1957-1966.
Huang et al. "Fully Humanized Neutralizing Antibodies to Interleukin-8 {ABX-ILB) Inhibit Angiogenesis, Tumor Growth, and Metastasis of Human Melanoma" American Journal of Pathology, , Jul. 2002, vol. 161, No. 1, pp. 125-134.
International Search Report and Written Opinion received for PCT Mar. 12, 2019, 10 pages.
Singh et al., "Targeting IL-8 signalling to inhibit breast cancer stem cell activity", Expert Opinion on Therapeutic Targets, 2013, vol. 17, No. 11, pp. 1235-1241.
Srivastava et al., "Interleukin-8 is a key mediator of FKBP51-induced melanoma growth, angiogenesis and metastasis", British Journal of Cancer, 2015, vol. 112, pp. 1772-1781.
Amey et al., "Targeting Cancer Stem Cells-A Renewed Therapeutic Paradigm", Cancer stem cells, 2017, vol. 13, pp. 15-55.
David et al., "The IL-8/IL-8R Axis: A Double Agent in Tumor Immune Resistance", Vaccines, 2016, vol. 4, No. 22, pp. 1-15.
Alfaro et al., "Tumor-Produced Interleukin-8 Attracts Human Myeloid-Derived Suppressor Cells and Elicits Extrusion of Neutrophil Extracellular Traps (NETs)", Clinical Cancer research, vol. 22, No. 15, Aug. 1, 2016, pp. 3924-3936.
International Preliminary Report on Patentability received for PCT Application Serial No. PCT/US2018/058037, dated May 14, 2020, 7 pages.
Notice of Allowance received for U.S. Appl. No. 16/174,040, dated, May 18, 2020, 7 pages.
Non-Final Office Action received for U.S. Appl. No. 16/174,040, dated, Jan. 31, 2020, 19 pages.
Genbank, "immunoglobulin G heavy chain variable region, partial [*Homo sapiens*]", AIT38746.1, Oct. 15, 2014, 1 page.
Genbank, "anti-rabies virus immunoglobulin light chain variable region, partial [*Homo sapiens*]", AAY33393.1, Jul. 26, 2016, 1 page.
Miller et al., "First-in-human' phase I dose escalation trial of IL-15N72D/IL-15Ra-Fc superagonist complex (AL T-803) demonstrates immune activation with anti-tumor activity in patients with relapsed hematological malignancy", Blood, Dec. 2015, vol. 126, No. 23, pp. 1-8.
Office Action received for Taiwanese Patent Application Serial No. 107138866 dated Mar. 9, 2020, 15 pages (Including English translation).
Office Action received for Canadian Patent Application Serial No. 3080429 dated Apr. 21, 2021, 6 pages.
Examination Report No. 1 received for Australian Patent Application Serial No. 2018359218 dated Jun. 18, 2021, 5 pages.
Extended European Search Report received for European Patent Application Serial No. 18872631.9 dated Jun. 24, 2021, 8 pages.
Galffy et al., "Inhibition of Interleukin-8 Reduces Human Malignant Pleural Mesothelioma Propagation in Nude Mouse Model", Oncology Research, 1999, vol. 11, pp. 187-194.
Mian et al., "Fully human anti-interleukin 8 antibody inhibits tumor growth in orthotopic bladder cancer xenografts via down-regulation of matrix metalloproteases and nuclear factor-kappaB", Clinical Cancer Research, 2003, vol. 9, pp. 3167-3175.
Examination Report No. 2 received for Australian Patent Application Serial No. 2018359218 dated Aug. 17, 2021, 3 pages.
Notice of Acceptance received for Australian Patent Application Serial No. 2018359218 dated Oct. 27, 2021, 3 pages.
Office Action received for Canadian Patent Application Serial No. 3,080,429 dated Mar. 16, 2022, 6 pages.
Notice of Reasons for Refusal received for Japanese Patent Application Serial No. 2020-524385 dated Sep. 30, 2022, 15 pages. (Including English Translation).
First Office Action received for Chinese Patent Application Serial No. 201880077692.6 dated Feb. 14, 2023, 11 pages. (Including English Translation).
Communication pursuant to Article 94(3) EPC received for EP Patent Applicaion Serial No. 18 872 631.9 dated Feb. 15, 2023, 5 pages.
Request for the Submission of an Opinion received for the Korean Patent Application Serial No. 10-2020-7015434 dated Mar. 9, 2023, 5 pages. (Including English Translation).
Notice of Allowance received for Canadian Patent Application Serial No. 3,080,429 dated Apr. 11, 2023, 1 page.
Notice of Reasons for Refusal received for Japanese Patent Application Serial No. 2020-524385 dated Mar. 31, 2023, 10 pages. (Including English Translation).
Decision of Refusal received for Japanese Patent Application Serial No. 2020-524385 dated Jul. 25, 2023, 10 pages. (Including English Translation).
Pre-Trial Reexamination Report received for Japanese Patent Application Serial No. 2020-524385 dated Jan. 5, 2024, 08 pages. (Including English Translation).
Non-Final Office Action received for U.S. Appl. No. 16/928,530 dated Nov. 2, 2022, 4 pages.
Notice of Allowance received for U.S. Appl. No. 16/928,530 dated May 10, 2023, 18 pages.
Office Action received for Taiwanese Patent Application Serial No. 107138866 dated Jul. 29, 2020, 15 pages (Including English translation).
Request for the Submission of an Opinion received for the Korean Patent Application Serial No. 10-2020-7015434 dated Sep. 22, 2022, 8 pages. (Including English Translation).
Decision to Grant received for the Korean Patent Application Serial No. 10-2020-7015434 dated Aug. 7, 2023, 13 pages. (Including English Translation).
Second Office Action received for Chinese Patent Application Serial No. 201880077692.6 dated Aug. 19, 2023, 13 pages. (Including English Translation).
Decision on Rejection Office Action received for Chinese Patent Application Serial No. 201880077692.6 dated Nov. 27, 2023, 13 pages. (Including English Translation).

(56) References Cited

OTHER PUBLICATIONS

Re-Examination Decision received for Chinese Patent Application Serial No. 201880077692.6 dated Apr. 1, 2024, 02 pages. (Including English Translation).
Office Action received for CA Application No. 3,080,429 dated Jun. 11, 2024, 03 pages.
Office Action received for EP Application No. 18872631.9 dated Nov. 15, 2024, 06 pages.
Qian Liu et al.,"The CXCL8-CXCR1/2 pathways in cancer", Cytokine &Growth Factor Reviews, 2016, pp. 61-67.
Dolgin Elie, "BMS bets on targeting IL-8 to enhance cancer immunotherapies", Nature Biotechnology, Oct. 2016, vol. 34, pp. 1006-1007.
Carlos Alfaro et al., "Carcinoma-Derived Interleukin-8 Disorients Dendritic Cell Migration Without Impairing T-Cell Stimulation", PLoS One, vol. 06, Mar. 2011, pp. 01-14.
Fourth Office Action received for Japanese Patent Application No. 2020-524385, dated Nov. 7, 2025, 10 pages including English translation.
Notice of Grant received for Australian Patent Application Serial No. 2018359218, dated Feb. 24, 2022, 1 page.
Notice of Grant received for Chinese Patent Application Serial No. 201880077692.6, dated Apr. 22, 2024, 4 pages including English Translation.
Notice of Grant received in Japanese Patent Application No. 2020-524385, dated Mar. 31, 2026, 4 pages including English translation.

* cited by examiner

| | ka | kd | Rmax | KD | Res sd |
|---|---|---|---|---|---|
| Il-8 (72mer) | 1.4e6 | 2.0e-4 | 21.7 | 147 pM | 0.181 |
| Il-8 (77mer) | 2.7e6 | 3.3e-4 | 22.9 | 120 pM | 0.251 |

43-12 pH7.4

| ka(M-1s-1) | koff(s-1) | KD |
|---|---|---|
| 1.9E+5 | 4.1E-4 | **2.1nM** |

pH6.0

| ka(M-1s-1) | koff(s-1) | KD |
|---|---|---|
| 4.2E+5 | 3.1E-3 | **7.4 nM** |

43-12a

| ka(M-1s-1) | koff(s-1) | KD |
|---|---|---|
| 1.0E+5 | 4.5E-5 | **0.47 nM** |

| ka(M-1s-1) | koff(s-1) | KD |
|---|---|---|
| 2.2E+5 | 9.7E-4 | **4.5 nM** |

43-12b

| ka(M-1s-1) | koff(s-1) | KD |
|---|---|---|
| 1.0E+5 | 2.0E-4 | **2.0 nM** |

| ka(M-1s-1) | koff(s-1) | KD |
|---|---|---|
| 3.3E+5 | 7.6E-4 | **2.3 nM** |

METHODS OF REDUCING EPITHELIAL-MESENCHYMAL TRANSITION WITH AN INTERLEUKIN-8 ANTIBODY

This application is a continuation of allowed U.S. patent application Ser. No. 16/928,530, which was filed on Jul. 14, 2020, which application is a divisional application of U.S. Pat. No. 10,752,682, which was filed Oct. 29, 2018, and which claims priority to U.S. Provisional patent application Ser. No. 62/580,232, which was filed Nov. 1, 2017. Each of these applications are incorporated by reference herein.

FIELD OF THE INVENTION

The field of the invention is compositions, methods, and use of recombinant scFv or antibody to interleukin-8 (IL-8) for treating a patient having a tumor to reduce metastasis of the tumor or to reduce immune suppression in the tumor microenvironment.

SEQUENCE LISTING

The content of the sequence listing named 102719.0009US3_ST26.XML, which is 48,105 Bytes in size was created on May 30, 2023 and electronically submitted along with the present application, and is incorporated by reference in its entirety.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Interleukin-8 (IL-8), also known as neutrophil chemotactic factor, is mainly produced by macrophages and epithelial cells, and has known to play a key role in immune system by recruiting immune cells (e.g., neutrophils) to the infection site. Recently, interest has been growing on identifying the relationship between the tumor-produced IL-8 and development of the tumor, especially in tumor metastasis and mechanism of immune-suppression in the tumor microenvironment. For example, several studies found that tumor-produced IL-8 is highly expressed in metastatic tumor cells and indeed, is capable of induce epithelial-mesenchymal transition of the tumor cells to produce tumor-initiating cells (e.g., tumor stem cells). Other studies showed that tumor-produced IL-8 attracts Myeloid-Derived Suppressor Cells (MDSC), which can provide immune-suppressive microenvironment around the tumor by interfering T-cell mediated immune response in the tumor microenvironment.

In order to mitigating the effect of IL-8 in tumor development, efforts had been put to neutralize tumor-expressed or endogenous IL-8 by providing human or humanized antibody against IL-8, anti-sense oligonucleotides or microRNA against IL-8. For example, U.S. Pat. Pub. No. 2003/0068319 to Bar-Eli discloses inhibition of angiogenesis and metastasis of tumor by fully humanized and isolated monoclonal or polyclonal IL-8. In another example, U.S. Pat. No. 5,849,903 to Petrzkowski teaches 20 base pair-length anti-sense oligonucleotide against IL-8 effective to reduce growth of melanoma or lung carcinoma. However, the effect of anti-sense oligonucleotides or microRNA may vary depending on the type of tumor, and the delivery method of such compositions. Also, isolated human or humanized antibody may not be effective in some tumor microenvironment where the isolated human or humanized antibodies are cleaved by endogenous metalloprotease in the tumor microenvironment.

Thus, even though several approaches of inhibiting expression or activity of IL-8 in tumor microenvironment have been studied, targeting IL-8 using recombinant IL-8 antibody or single chain variable fragment (scFv) with amino acid sequences of high affinity to IL-8 has remained largely unexplored. Therefore, there is still a need for improved compositions, methods for and uses of recombinant IL-8 antibody or single chain variable fragment (scFv) to target tumor-expressed or endogenous IL-8 in the tumor microenvironment to promote effect of cancer therapy.

SUMMARY OF THE INVENTION

The inventive subject matter is directed to various compositions of, methods for, and uses of a recombinant IL-8 antibody, single chain variable fragment (scFv), or other portion of an antibody (including fusion products, especially in a T×M) with high affinity to IL-8 to target tumor-expressed or endogenous IL-8 and neutralize the effect of IL-8 in promoting EMT (epithelial-mesenchymal transition) of a tumor cell, and/or immune-suppression in the tumor microenvironment. Consequently, the scFv peptides may be coupled to a protein having IL-15 activity and/or to a protein having IL-15 receptor alpha activity to so form a T×M molecule.

Thus, one aspect of the subject matter includes single chain variable fragment (scFv) peptide. The scFv peptide includes a $V_H$ segment comprising a first amino acid sequence and/or a $V_L$ segment comprising a second amino acid sequence. The first and second amino acid sequences are selected from SEQ ID NO. 1-15, 31-32 or SEQ ID NO. 16-30, 33-34, respectively.

In another aspect of the inventive subject matter, the inventors contemplate a pharmaceutical composition for treating a patient having a cancer. The pharmaceutical composition includes single chain variable fragment (scFv) having includes a $V_H$ segment comprising a first amino acid sequence and/or a $V_L$ segment comprising a second amino acid sequence. The first and second amino acid sequences are selected from SEQ ID NO. 1-15, 31-32 or SEQ ID NO. 16-30, 33-34, respectively. Preferably, the scFv peptide is present in the pharmacologically acceptable carrier.

Still another aspect of inventive subject matter is directed towards a recombinant nucleic acid. The recombinant nucleic acid includes a first nucleic acid segment encoding a $V_H$ segment having a first amino acid sequence selected from the group consisting of SEQ ID NO. 1-15, 31-32 and/or a second nucleic acid segment encoding a $V_L$ segment having a second amino acid sequence selected from the group consisting of SEQ ID NO. 16-30, 33-34. Optionally, the first and second segments are present in a same reading frame.

In still another aspect of the inventive subject matter, the inventors contemplate a recombinant isolated antibody or fragment thereof. The recombinant isolated antibody or fragment thereof includes a $V_H$ domain and/or a $V_L$ domain having respective first and second amino acid sequences. Preferably, the first amino acid sequence is at least 95% identical to a third amino acid sequence selected from the group consisting of SEQ ID NO. 1-15, 31-32, and the second amino acid sequence is at least 95% identical to a third amino acid sequence selected from the group consisting of SEQ ID NO. 16-30, 33-34.

In still another aspect of the inventive subject matter, the inventors also contemplate a method of reducing an IL-8 effect in a tissue. In this method, a single chain variable fragment (scFv) having includes a $V_H$ segment comprising a first amino acid sequence and/or a $V_L$ segment is provided. Preferably, the first amino acid sequence is at least 95% identical to a third amino acid sequence selected from the group consisting of SEQ ID NO. 1-15, 31-32, and the second amino acid sequence is at least 95% identical to a third amino acid sequence selected from the group consisting of SEQ ID NO. 16-30, 33-34. The method continues with a step of treating the tissue with the scFv peptide in a dose and schedule effective to reduce the IL-8 effect in the tissue.

In still another aspect of the inventive subject matter, the inventors contemplate a method of treating a patient having a tumor. In this method, a pharmaceutical composition including a single chain variable fragment (scFv) having a $V_H$ segment comprising a first amino acid sequence and/or a $V_L$ segment is provided. Preferably, the first amino acid sequence is at least 95% identical to a third amino acid sequence selected from the group consisting of SEQ ID NO. 1-15, 31-32, and the second amino acid sequence is at least 95% identical to a third amino acid sequence selected from the group consisting of SEQ ID NO. 16-30, 33-34. The pharmaceutical composition is administered to the patient in a dose and a schedule effective to treat the tumor.

In still another aspect of the inventive subject matter, the inventors contemplate a method of reducing immune suppression in a patient having a tumor. In this method, a pharmaceutical composition including a single chain variable fragment (scFv) having a $V_H$ segment comprising a first amino acid sequence and/or a $V_L$ segment is provided. Preferably, the first amino acid sequence is at least 95% identical to a third amino acid sequence selected from the group consisting of SEQ ID NO. 1-15, 31-32, and the second amino acid sequence is at least 95% identical to a third amino acid sequence selected from the group consisting of SEQ ID NO. 16-30, 33-34. The pharmaceutical composition is administered to the patient in a dose and a schedule effective to reduce presence of myeloid-derived suppressor cells in a tumor microenvironment.

In still another aspect of the inventive subject matter, the inventors contemplate a method of reducing Th-2 mediated immune response in a patient having a tumor. In this method, a pharmaceutical composition including a single chain variable fragment (scFv) having a $V_H$ segment comprising a first amino acid sequence and/or a $V_L$ segment is provided. Preferably, the first amino acid sequence is at least 95% identical to a third amino acid sequence selected from the group consisting of SEQ ID NO. 1-15, 31-32, and the second amino acid sequence is at least 95% identical to a third amino acid sequence selected from the group consisting of SEQ ID NO. 16-30, 33-34. The pharmaceutical composition is administered to the patient in a dose and a schedule effective to reduce Th-2 mediated immune response in the patient.

In still another aspect of the inventive subject matter, the inventors contemplate a method of reducing epithelial-mesenchymal transition of a tumor cell in a patient. In this method, a pharmaceutical composition including a single chain variable fragment (scFv) having a $V_H$ segment comprising a first amino acid sequence and/or a $V_L$ segment is provided. Preferably, the first amino acid sequence is at least 95% identical to a third amino acid sequence selected from the group consisting of SEQ ID NO. 1-15, 31-32, and the second amino acid sequence is at least 95% identical to a third amino acid sequence selected from the group consisting of SEQ ID NO. 16-30, 33-34. The pharmaceutical composition is administered to the patient in a dose and a schedule effective to reduce epithelial-mesenchymal transition of the tumor cell.

In still another aspect of the inventive subject matter, the inventors contemplate use of the scFv peptide described above for reducing Th-2 mediated immune response in a patient having a tumor. Also, the inventors contemplate use of the scFv peptide described above for reducing epithelial-mesenchymal transition of a tumor cell in a patient. In addition, the inventors further contemplate use of the scFv peptide described above for reducing metastasis of a tumor in a patient having the tumor.

Various objects, features, aspects and advantages of the inventive subject matter will become more apparent from the following detailed description of preferred embodiments, along with the accompanying drawing.

DETAILED DESCRIPTION

Figure 1A:
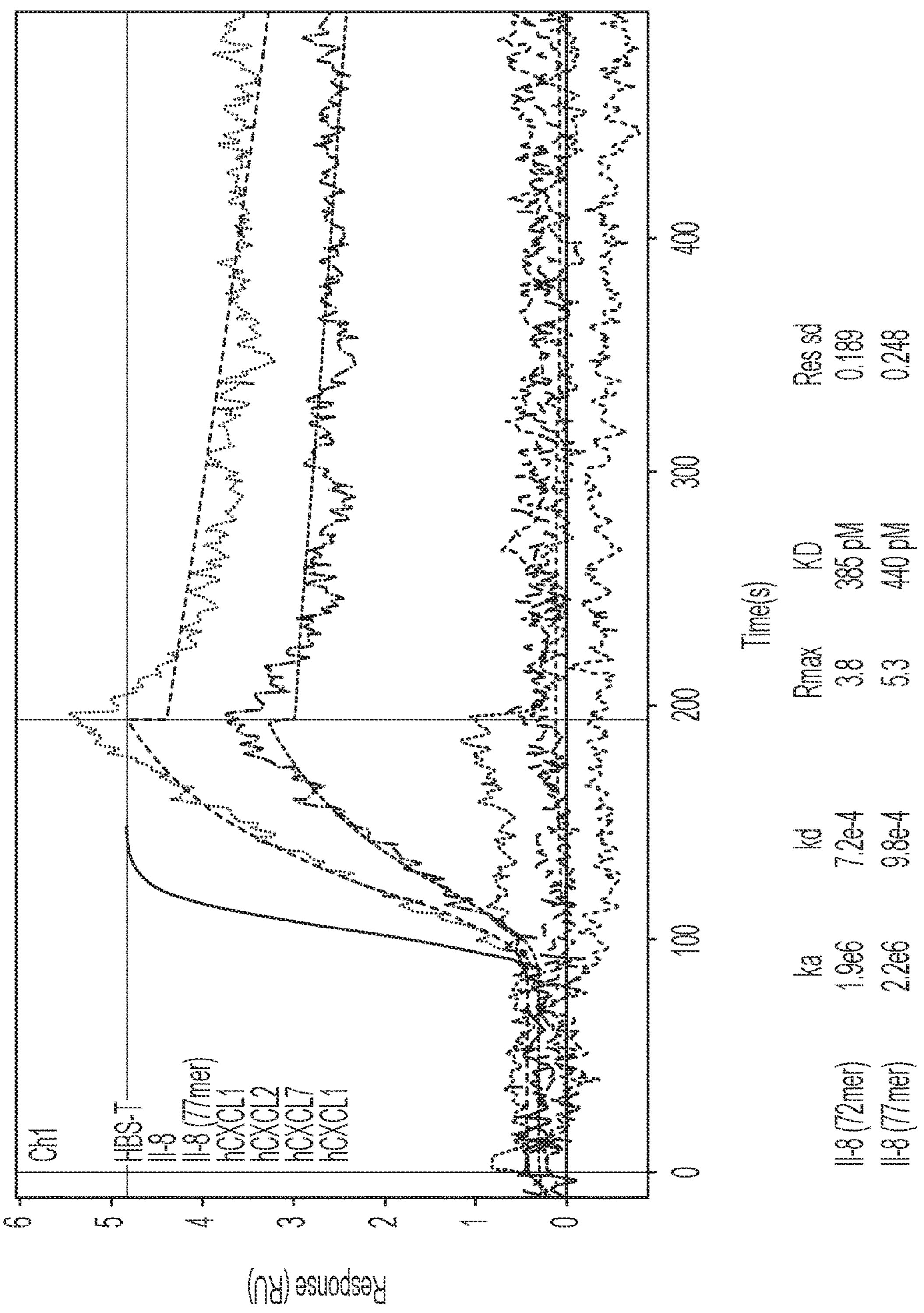
FIG. 1A shows a graph of binding kinetics between one of scFv peptide (43-12) with IL-8 or IL-8 orthologs or paralogs.

The inventors now discovered that various IL-8 mediated effects, including tumor development, particularly IL-8 mediated tumor metastasis through epithelial-mesenchymal transition pathway, can be significantly reduced or even abrogated by mitigating the IL-8 effect. Such mitigating effect can be achieved by trapping or otherwise binding IL-8 in the tumor microenvironment using a recombinant IL-8 antibody or fragments thereof (e.g., scFv fragment against IL-8 with high affinity against IL-8).

To that end, the inventors discovered that various recombinant antibody or fragments thereof such as a scFv with high affinity against IL-8 can be generated such that recombinant antibody or fragments thereof, or scFv fragments can trap tumor-generated or endogenous IL-8 in the tumor microenvironment. Binding or entrapment of IL-8 from the tumor microenvironment is thought to decrease the IL-8 effect to the tumor cells triggering metastasis of the tumor cells. Also, binding or entrapment of IL-8 can reduce the IL-8 effect of increasing immune suppression in the tumor microenvironment via accumulating myeloid-derived suppressor cells (MDSC). Further, binding or entrapment of IL-8 can reduce the IL-8 effect of increasing Th2-mediated immune response in the tumor microenvironment, which can contribute to recruitment of myeloid-derived suppressor cells in the tumor microenvironment. While not wishing to be bound by any specific theory or hypothesis, it is contemplated that IL-8 bund to an antibody or fragment will no longer be able to exert its biological signaling function, possibly due to steric effects. Moreover, where binding is mediated on a particle or other surface to so entrap the IL-8, IL-8 concentrations needed for signaling may be reduced and so reduce or abrogate IL-8 effects. Thus, the terms binding and entrapment are used interchangeably herein.

As used herein, the term "tumor" refers to, and is interchangeably used with one or more cancer cells, cancer tissues, malignant tumor cells, or malignant tumor tissue, that can be placed or found in one or more anatomical locations in a human body.

As used herein, the term "bind" refers to, and can be interchangeably used with a term "recognize" and/or "detect", an interaction between two molecules with a high affinity with a $K_D$ of equal or less than $10^{-3}$M, $10^{-4}$M, $10^{-5}$M, $10^{-6}$M, or equal or less than $10^{-7}$M.

As used herein, the term "provide" or "providing" refers to and includes any acts of manufacturing, generating, placing, enabling to use, or making ready to use.

In one exemplary and especially preferred aspect of the inventive subject matter, the inventors contemplate a single chain variable fragment (scFv) peptide having a $V_H$ segment and a $V_L$ segment that binds to IL-8. While it is contemplated that the peptide sequence of scFv can be any suitable sequences providing desirable binding affinity to IL-8, the inventors found that the scFv peptide can be generated using at least one or more of peptide sequences in Table 1: SEQ ID: 1-34.

Alternatively and additionally, the inventors also contemplate that the amino sequences of $V_H$ segments and/or $V_L$ segments presented in Table 1 can be used to generate a recombinant, isolated antibody or fragment thereof. As used herein, the term "antibody" refers to immunoglobulin molecules and immunologically active portions of immunoglobulin molecules, i.e., molecules that contain an antigen-binding site that immune-specifically bind an antigen. Thus, "antibody and the fragment thereof" includes a whole immunoglobulin molecule (e.g., a full-size, whole $IgG_1$, etc.), a fragment of the whole antibody molecule. Thus, the fragment thereof may include, but not limited to, scFv, Fab fragments, Fab' fragments, F(ab')2, disulfide linked Fvs (sdFvs), Fvs, and any fragment comprising either $V_H$ segment and/or $V_L$ segment. Where the antibody is an immunoglobulin, it is contemplate that the immunoglobulin can include any type (e.g., IgG, IgE, IgM, IgD, IgA and IgY) and any class (e.g., IgG1, IgG2, IgG3, IgG4, IgA1 and IgA2) of heavy chain or constant domain to constitute different types of immunoglobulin. In addition, the "antibody" can include, but not limited to a human antibody, a humanized antibody, a chimeric antibody, a monoclonal antibody, a polyclonal antibody. Thus, it should be appreciated that the $V_H$ and/or $V_L$ domains as shown in Table 1 can be grafted into any existing (typically human or humanized) antibody or antibody fragment using methods well known in the art.

The inventors further contemplated that the that the amino sequences of $V_H$ segments and/or $V_L$ segments presented in Table 1 can be used coupled with a carrier protein to generate a hybrid protein having the $V_H$ segments and/or $V_L$ segments on its surface such that IL-8 can be captured by the hybrid protein. Any suitable form of carrier protein that can stably carry $V_H$ segments and/or $V_L$ segments and preferably provide an access to the tumor microenvironment is contemplated. One especially preferred carrier protein includes albumin, refolded albumin, and other proteins with affinity to antibody portions (e.g., protein A, protein G, protein Z) coupled with one or more $V_H$ segments and/or $V_L$ segments.

Typically, $V_H$ segments and/or $V_L$ segments are coupled with an anchor molecule by which $V_H$ segments and/or $V_L$ segments can be coupled with the carrier protein. For example, where the carrier protein is an albumin, the anchor molecule can be a hydrophobic peptide or glycolipids in any suitable size to fit in one of Sudlow's site I and II of the albumin or any other hydrophobic area of the albumin. For example, the recombinant immunoglobulin protein against IL-8 as described above can be coupled with the carrier protein via its Fc domain. In other embodiments, the anchor molecule may include a hydrophobic peptide (in a length of at least 10 amino acids, 15 amino acids, 20 amino acids, 30 amino acids, etc.). In these embodiments, various configurations of $V_H$ segments and/or $V_L$ segments (e.g., as a form of scFv) and hydrophobic peptides can be contemplated. For example, a monovalent scFv domain can be directly linked to a hydrophobic peptide, or a multivalent scFv can be directly linked to a hydrophobic peptide. Alternatively, one scFv domain can be directly linked to a plurality of hydrophobic peptides or a plurality of scFv domain can be directly linked to a plurality of hydrophobic peptides.

Alternatively, or additionally, one or more $V_H$ segments and/or $V_L$ segments can be coupled with an intermediate molecule that has an anchor portion to bind to the carrier protein. In a preferred embodiment, the inventors contemplate that the intermediate molecule provides a plurality of binding sites for $V_H$ segments and/or $V_L$ segments such that multiple target recognition domains can be carried via a single binding site on the carrier protein. Suitable intermediate molecule may include any protein, glycolipid, organic molecule, or inorganic molecule that does not provide any significant toxicity to the naïve tissue. For example, the suitable intermediate molecule may include a nanoparticle (e.g., quantum dots, gold nanoparticles, magnetic nanoparticles, nanotubes, polymeric nanoparticles, dendrimers, etc.), or a bead (e.g., polystyrene bead, latex bead, dynabead, etc.). Preferably, the nanoparticle and/or beads have a dimension below 1 m, preferably below 100 nm. The nanoparticle may be crosslinked to or partially coated with a hydrophobic tail that provide an anchor to the carrier protein (e.g., albumin). One or more $V_H$ segments and/or $V_L$ segments can be also crosslinked to or partially coated on the nanoparticles (e.g., via an extra tail domain linked to the target recognition domain for crosslinking, etc.).

In another example, suitable intermediate molecules may include beads (e.g., polystyrene beads, latex beads, dynabeads, etc.) coupled with an antibody against the carrier protein. Thus, where the carrier protein is an albumin, the beads can be coupled (e.g., crosslinked, coated, etc.) with α-albumin antibody such that the bead can bind to the carrier protein with a high affinity and specificity. One or more $V_H$ segments and/or $V_L$ segments can be also crosslinked to or partially coated on the bead (e.g., via an extra tail domain linked to the target recognition domain for crosslinking, thiol-mediated crosslinking, etc.).

In some embodiments, scFv peptide can form a recombinant immunoglobulin protein complex that comprises or mimics an ALT-803 (IL-15 superagonist complex, see e.g., *Blood* 2015 126:1957) or T×M (targeted ALT-803-based scaffold platform, see e.g., URL altorbioscience.com/our-science/il-15-protein-superagonist-and-scaffold-technology/) structure. Preferably, the inventors contemplate that, where the immunoglobulin protein complex mimics T×M structure, the scFv peptide can be directly (or indirectly via a linker) coupled to one or more interleukin-15 (IL-15) binding motif, and/or one or more ligand to the IL-15 binding motif (e.g., IL-15, IL-15N72D, etc.). Viewed from a different perspective, the scFv peptide may be coupled to a protein having IL-15 activity or to a protein having IL-15 receptor alpha activity. Thus, where the recombinant immunoglobulin protein complex mimics a T×M $IgG_1$ structure, the recombinant immunoglobulin protein complex may include 1-4 scFv peptides against IL-8.

Additionally, the recombinant immunoglobulin protein complex mimicking T×M structure having one or more scFv peptide coupled with IL-15 binding motif or its ligand may also include a binding domain against a tumor specific antigen or patient- and tumor specific neoepitope (e.g., an scFv peptide against the neoepitope, etc). For example, the recombinant immunoglobulin protein complex may include two scFv peptides against IL-8 coupled with two IL-15 binding motives and two ScFv peptides against the neoepitope coupled with two IL-15 binding motif ligands. Preferably, the neoepitope is patient-specific and tumor-specific, which is identified by omics analysis of the sequence data as disclosed in US 2012/0059670A1 and US 2012/0066001A1.

In some embodiments, the scFv, recombinant antibody or fragment thereof, can be generated using one sequence encoding a $V_H$ segment among SEQ ID No. 1-15, 31-32. In other embodiments, the scFv, recombinant antibody or fragment thereof, can be generated using one sequence encoding a $V_L$ segment among SEQ ID No. 16-30, 33-34. In still other embodiments, the scFv, recombinant antibody or fragment thereof, can be generated using one sequence encoding a $V_H$ segment among SEQ ID No. 1-15, 31-32 and one sequence encoding a $V_L$ segment among SEQ ID No. 16-30, 33-34. In these embodiments, it is preferred that the sequence encoding the $V_H$ segment and sequence encoding the $V_L$ segment are the paired one (e.g., SEQ ID NO. 1 and 16 for scFv 49-31, SEQ ID NO. 2 and 17 for scFv 49-22, SEQ ID NO. 3 and 18 for scFv 49-7, etc.). However, it is contemplated that any pair of $V_H$ segment and $V_L$ segment can be generated by selecting one $V_H$ segment from SEQ ID No. 1-15, 31-32 and one $V_L$ segment from SEQ ID No. 16-30, 33-34.

TABLE 1

| SEQ ID No. | Seq name | Amino Acid Sequences |
|---|---|---|
| 1 | 49-31 $V_H$ | EVQLVESGGGLVQPGGSLRLSCAASGFTFSSYYMHWVRQAPGKGLEWVSAIS GGGSSTYYADSVKGRFTISRDNSKNTLYLQMNSLRAEDTAVYYCARDLRIFEG RDAGFDVWGQGTLVTVS |
| 2 | 49-22 $V_H$ | EVQLVESGGGLVQPGGSLRLSCAASGFTFTSYAMHWVRQAPGKGLEWVSAIS GSGGSTYYADSVKGRFTISRDNSKNTLYLQMNSLRAEDTAVYYCARDLDMFV PFWPAFDVWGQGTLVTVSS |
| 3 | 49-7 $V_H$ | EVQLVESGGGLVQPGGSLRLSCAASGFTFSSYAMHWVRQAPGKGLEWVSAIS NSGASTYYADSVKGRFTISRDNSKNTLYLQMNSLRAENTAVYYCARDLMRW WIDGFDVWGQGTLVTVSS |
| 4 | 49-32 $V_H$ | EVQLVESGGGLVQPGGSLRLSCAASGFTFSSYAMHWVRQAPGKGLEWVSAIY GNGGSTYYADSVKGRFTISRDNSKNTLYLQMNSLRAEDTAVYYCARDLYTIEP REAFDVWGQGTLVTVSS |
| 5 | 49-34 $V_H$ | EVQLVESGGGLVQPGGSLRLSCAASGFTLGSYAMHWVRQAPGKGLEWVSAIS GSGGSTYYADSVKGRFTISRDNSKNTLYLQMNSLRAEDTAVYYCARDRDTVSI EVGFDVWGQGTLVTVSS |
| 6 | 49-18 $V_H$ | EVQLVESGGGLVQPGGSLRLSCAASGFTFSSYAMNWVRQAPGKGLEWVSAIS WSGGNTYYADSVKGRFTISRDNSKNTLYLQMNSLRAEDTAVYYCARDLYAG YWGFDVWGQGTLVTVSS |
| 7 | 49-3 $V_H$ | EVQLVESGGGLVQPGGSLRLSCAASGFTFSSYAMTWVRQAPGKGLEWVSVIS GSGGSTRYADSVKGRFTISRDNSKNTLYLQMNSLRAEDTAVYYCARDRKFPY VQFFRNGFDVWGQGTLVTVSS |
| 8 | 43-2 $V_H$ | EVQLVESGGGLVQPGGSLRLSCAASGFTFSSYAMHWVRQAPGKGLEWVSAIS GSGGKTYYADSVKGRFTISRDNSKNTLYLQMNSLRAEDTAVYYCARDREAPF YTVYVTGFDVWGQGTLVTVSS |
| 9 | 49-37 $V_H$ | EVQLVESGGGLVQPGGSLRLSCAASGFTFSSYAMNWVRQAPGKGLEWVSAIS YSGGSTYYADSVKGRFTISRDNSKNTLYLQMNSLRAEDTAVYYCARDLWLG WWGFDVWGQGTLVTVSS |
| 10 | 43-12 $V_H$ | EVQLVESGGGLVQPGGSLRLSCAASGFTFSSYLMHWVRQAPGKGLEWVSAIS GSGGSTYYADSVKGRFTISRDNSKNTLYLQMNSLRAEDTAVYYCARDREGWF WHSYGFDVWGQGTLVTVSS |
| 11 | 49-10 $V_H$ | EVQLVESGGGLVQPGGSLRLSCAASGFTFSSYAMNWVRQAPGKGLEWVSAIS GSGGSTYYADSVKGRFTISRDNSKNTLYLQMNSLRAEDTAVYYCARDLGWLS RLFAGFDVWGQGTLVTVSS |
| 12 | 49-1 $V_H$ | EVQLVESGGGLVQPGGSLRLSCAASGFTFSSYWMHWVRQAPGKGLEWVSAIS WSGGSTSYADSVKGRFTISRDNSKNTLYLQMNSLRAEDTAVYYCARDLTWW VQAFDVWGQGTLVTVSS |

TABLE 1-continued

| SEQ ID No. | Seq name | Amino Acid Sequences |
|---|---|---|
| 13 | 49-6 $V_H$ | EVQLVESGGGLVQPGGSLRLSCAASGFTFSEYAMHWVRQAPGKGLEWVSAID<br>GNGTSTYYADSVKGRFTISRDNSKNTLYLQMNSLRAEDTAVYYCARDRDTAL<br>ETGFDVWGQGTLVTVSS |
| 14 | 49-12 $V_H$ | EVQLVESGGGLVQPGGSLRLSCAASGFTFSSYYMHWVRQAPGKGLEWVSAIS<br>NSGGSTHYADSVKGRFTISRDNSKNTLYLQMNSLRAEDTAVYYCARDLWWL<br>PAFDVWGQGTLVTVSS |
| 15 | 49-25 $V_H$ | EVQLVESGGGLVQPGGSLRLSCAASGFTFSSYAMNWVRQAPGKGLEWVSAIS<br>WSGGRTYYADSVKGRFTISRDNSKNTLYLQMNSLRAEDTAVYYCARDLYDG<br>VWGFDVWGQGTLVTVSS |
| 16 | 49-31 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQDDDVPWTFGQGTKVEIK |
| 17 | 49-22 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQASDTPLTFGQGTKVEIK |
| 18 | 49-7 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQSYDIPLTFGQGTKVEIK |
| 19 | 49-32 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQDYTSPLTFGQGTKVEIK |
| 20 | 49-34 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQDSAFPLTFGQGTKVEIK |
| 21 | 49-18 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQDYGYPLTFGQGTKVEIK |
| 22 | 49-3 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQHTNGPFTFGQGTKVEIK |
| 23 | 43-2 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQDADTPLTFGQGTKVEIK |
| 24 | 49-37 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQYNTIPYTFGQGTKVEIK |
| 25 | 43-12 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQVYSGPWTFGQGTKVEIK |
| 26 | 49-10 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQDYGYPLTFGQGTKVEIK |
| 27 | 49-1 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQVDDSPLTFGQGTKVEIK |
| 28 | 49-6 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQDNAFPLTFGQGTKVEIK |
| 29 | 49-12 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQSSGWPFTFGQGTKVEIK |
| 30 | 49-25 $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQYSSYPFTFGQGTKVEIK |
| 31 | 43-12a $V_H$ | EVQLVESGGGLVQPGGSLRLSCAASGFTFSSYLMHWVRQAPGKGLEWVSAIS<br>GSGGITYYADSVKGRFTISRDNSKNTLYLQMNSLRAEDTAVYYCARDREGWF<br>WHSYGFDVWGQGTLVTVSS |
| 32 | 43-12b $V_H$ | EVQLVESGGGLVQPGGSLRLSCAASGFTFSSYLMHWVRQAPGKGLEWVSAIS<br>GSGGITYYADSVKGRFTISRDNSKNTLYLQMNSLRAEDTAVYYCARDREGWF<br>WHSYGFDVWGQGTLVTVSS |
| 33 | 43-12a $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQVYSGPWTFGQGTKVEIK |
| 34 | 43-12b $V_L$ | DIQMTQSPSSLSASVGDRVTITCQASQDISNYLNWYQQKPGKAPKLLIYDASNL<br>ETGVPSRFSGSGSGTDFTFTISSLQPEDIATYYCQQTYSGPWTFGQGTKVEIK |

The inventors also contemplate that the scFv, recombinant antibody or fragment thereof, can be generated with amino acid sequences encoding $V_H$ segment and/or $V_L$ segment that are at least 85% identical, preferably at least 90% identical, more preferably at least 95% identical to any one of SEQ ID No. 1-15, 31-32 or to any one of SEQ ID No.

16-30, 33-34, respectively. In such embodiment, it is preferred that the binding affinity of the scFv peptide, recombinant antibody or fragment thereof, is no less than 60%, preferably no less than 70%, more preferably no less than 80% of binding affinity of a scFv peptide, recombinant antibody or fragment thereof, generated with any one of SEQ ID No. 1-15, 31-32 or to any one of SEQ ID No. 1-15, 31-32. Indeed, and as discussed in further detail below, the inventors used a selected scFv (43-12) and subjected the scFv to affinity maturation via random mutagenesis in the CDR regions for $V_H$ and $V_L$. Notable, and among other binders, two scFv (43-12a and 43-12b) were isolated from the affinity maturation process that had improved binding characteristics.

Most typically, the $V_H$ segment and $V_L$ segment in scFv peptide, recombinant antibody or fragment thereof, are coupled via a linker or a spacer, which is typically between 5-40 amino acids, preferably between 10-30 amino acids, more preferably between 20-30 amino acids. In some embodiments, the linker can couple the N-terminus of $V_H$ segment and C-terminus of $V_L$ segment. In other embodiments, the linker can couple the N-terminus of $V_L$ segment and C-terminus of $V_H$ segment. The inventors contemplate that glycine-rich sequences (e.g., $(G_4S)_n$, with n between 1-5, etc.) for the linker are preferred to provide structural flexibility between the $V_H$ segment and $V_L$ segments. It is also contemplated that the linker includes one or more serine or threonine residue to increase solubility of the scFv peptide, recombinant antibody or fragment thereof. There are numerous linkers and methods of making scFv known in the art, and all such known methods are deemed suitable for use herein.

Additionally, the scFv peptide can include a plurality of $V_H$ segments and $V_L$ segments to form a divalent or multivalent scFv. In some embodiments, the plurality of $V_H$ segments and/or $V_L$ segments may have same amino sequences (e.g., a multivalent scFv having three $V_H$ segments and three $V_L$ segments, and all $V_H$ segments have 49-31 $V_H$ (SEQ ID. No. 1) and all $V_L$ segments have 49-31 $V_L$ (SEQ ID. No. 16). In other embodiments, at least two of $V_H$ segments and/or $V_L$ segments may have different amino acid sequences (e.g., a multivalent scFv having three $V_H$ segments and three $V_L$ segments, and two of $V_H$ segments are 49-31 $V_H$ (SEQ ID. No. 1) and one of $V_H$ segments is 49-22 $V_H$ (SEQ ID. No. 2), and two of $V_L$ segments are 49-31 $V_L$ (SEQ ID. No. 16) and one of $V_H$ segments is 49-22 $V_L$ (SEQ ID. No. 17).

Preferably, the binding affinity (Kd) of the scFv, recombinant antibody or fragment thereof, to IL-8 (at least one of 72-mer and 77-mer IL-8) is at least less than $1\times10^{-7}$M, preferably less than $1\times10^{-8}$M, and more preferably less than $1\times10^{-9}$M, measured at a temperature between 25° C. to 37° C., and measured in a pH range between 5.5-7.5. The inventors contemplate that the binding affinities of the scFv, recombinant antibody or fragment thereof, to IL-8 may be different due to the structural differences even if the scFv, recombinant antibody or fragment thereof, are generated using the same amino acid sequences of $V_H$ segment and/or $V_L$ segments. For example, Table 2 provides different affinities (measured in KD value) of scFv and recombinant antibody (IgG1) of several clones. Clone 49-31 is a scFv or a recombinant antibody (IgG1) generated using amino acid sequences encoding $V_H$ segment (SEQ ID No. 1) and $V_L$ segment (SEQ ID No. 16), Clone 43-2 is a scFv or a recombinant antibody (IgG1) generated using amino acid sequences encoding $V_H$ segment (SEQ ID No. 8) and $V_L$ segment (SEQ ID No. 23), and Clone 43-12 is a scFv or a recombinant antibody (IgG1) generated using amino acid sequences encoding $V_H$ segment (SEQ ID No. 10) and $V_L$ segment (SEQ ID No. 25). Preliminary $K_D$ values are determined by surface plasmon resonance measurement, and highest and lowest values are shown to estimate the range of the affinities to IL-8. All unit of Kd value in Table 2 is $10^{-9}$ M.

TABLE 2

| Clone | scFv | IgG1 (25° C., pH 7.4) | IgG1 (25° C., pH 6.0) | IgG1 (37° C., pH 7.4) |
|---|---|---|---|---|
| 49-31 | 0.009-0.048 | 0.009-0.25 | 0.21-0.22 | 0.117 |
| 43-2 | 1.41 | 0.79 | 0.30-0.96 | 0.72-0.89 |
| 43-12 | 1.50 | 0.43-0.78 | 3.46-6.7 | 0.31 |

Table 3 provides further exemplary data for molecules having sequences as shown in Table 1. Here, scFv and corresponding humanized $IgG_1$ were prepared using the sequences as indicated, and KD was determined using SPR with immobilized IL-8 as the analyte on the chip surface. All values are expressed as nanoM values at temperatures as indicated.

TABLE 3

| Clone | scFv (25° C.) | IgG1 (25° C.) | IgG (37° C.) |
|---|---|---|---|
| 49-31 | 0.009-0.048 | 0.099-0.25 | 0.12 |
| 49-22 | 0.11-0.114 | | |
| 49-7 | 0.087-0.17 | | |
| 49-32 | 0.21-0.24 | 0.77-0.87 | 0.33-0.36 |
| 49-34 | 0.44-0.62 | | |
| 49-18 | 0.41-0.89 | | |
| 49-3 | 1.26 | 2.14 | 9.19 |
| 43-2 | 1.41 | 0.79 | 0.72-0.89 |
| 49-37 | 1.12-1.46 | | |
| 43-12 | 1.50 | 0.43-0.78 | 0.31 |
| 49-10 | 1.65 | 2.21 | 3.45 |
| 49-1 | 2.66 | | |
| 49-6 | 4.8 | | |
| 49-12 | 10.1 | | |
| 49-25 | 25.0 | | |

It is further contemplated that the scFv peptide (or $V_H$ segment and $V_L$ segment of an antibody or fragment thereof) can be encoded by a single recombinant nucleic acid. In this embodiment, the recombinant nucleic acid includes at least two nucleic acid segments: a first nucleic acid segment (a sequence element) encoding a $V_H$ segment and a second nucleic acid segment encoding a $V_L$ segment. It is preferred that the first nucleic acid segment is selected to encode at least one of amino acid sequences of SEQ ID. No 1-15, 31-32, and the second nucleic acid segment is selected to encode at least one of amino acid sequences of SEQ ID. No 16-30, 33-34. However, it is also contemplated that the first and second nucleic acid segment encode $V_H$ and $V_L$ segment respectively that are at least 85% identical, preferably at least 90% identical, more preferably at least 95% identical to any one of SEQ ID No. 1-15, 31-32 or to any one of SEQ ID No. 16-30, 33-34. Most preferably, the two nucleic acid segments are in the same reading frame such that two nucleic acid segments can be translated into a single protein having two peptide segments.

Additionally, the recombinant nucleic acid may include a third nucleic acid segment between the first and second nucleic acid segment encoding a linker peptide (preferably G-rich or otherwise flexible linker peptide), which is typically between 5-40 amino acids, preferably between 10-30 amino acids, more preferably between 20-30 amino acids. In this embodiment, it is especially preferred that the three nucleic acid segments are in the same reading frame such that three nucleic acid segments can be translated into a single protein having three peptide segments.

In some embodiments, the recombinant nucleic acid may include a plurality of sets of first and second nucleic acid segments, in which each set includes one of each first and second nucleic acid segment. In these embodiments, the recombinant nucleic acid preferably includes a fourth nucleic acid segment encoding a connector peptide located between each set of the first and second nucleic acid segments. Thus, one exemplary recombinant nucleic acid may include [first set]-fourth nucleic acid encoding a connector peptide-[second set]-fourth nucleic acid encoding the connector peptide-[third set], where each of first, second, and third set includes [a first nucleic acid encoding $V_H$ segment-a third nucleic acid encoding a linker-a second nucleic acid encoding $V_L$ segment], where the location of the first and second nucleic acid can be alternated with each other. The sequence of the connector peptide may vary depending on the number of sets in a single peptide. Preferably, the connector peptide may be between 5-50 amino acids, preferably between 10-40 amino acids, more preferably between 20-30 amino acids. Also inventors contemplates that glycine-rich sequences (e.g., $G_4S$, etc.) are preferred to provide flexibility of the connector peptide between the $V_H$ and $V_L$ segment sets.

The inventors further contemplate that the scFv peptide, antibodies or fragments thereof, can be formulated as a pharmaceutical composition so that it can be administered to the patient having a tumor to reduce or inhibit the endogenous effect of IL-8. Therefore, it is contemplated that the scFv peptide, antibodies or fragments thereof, can be formulated in any pharmaceutically acceptable carrier (e.g., as a sterile injectable composition) in an amount of at least 1 ml, preferably at least 5 ml, more preferably and at least 20 ml per dosage unit for a therapeutic formulation. However, alternative formulations are also deemed suitable for use herein, and all known routes and modes of administration are contemplated herein. As used herein, the term “administering” refers to both direct and indirect administration of the compounds and compositions contemplated herein, where direct administration is typically performed by a health care professional (e.g., physician, nurse, etc.), while indirect administration typically includes a step of providing or making the compounds and compositions available to the health care professional for direct administration.

In some embodiments, the pharmaceutical formulation is administered via systemic injection including subcutaneous, subdermal injection, or intravenous injection. In other embodiments, where the systemic injection may not be efficient (e.g., for brain tumors, etc.), it is contemplated that the formulation is administered via intratumoral injection.

One exemplary method and use of pharmaceutical composition including scFv peptide, the antibody or fragment thereof, which includes $V_H$ and $V_L$ segments described above is to reduce IL-8 mediated effects in a target tissue. As used herein, the IL-8 mediated effect refers to any biological consequence induced directly or indirectly by presence of IL-8 in the tissue or the microenvironment of the tissue. Thus, the IL-8 effect may be originated from IL-8 released (or secreted) by a tumor cell and/or a non-tumor cell in the tissue (e.g., immune competent cell such as lymphocytes etc.) or outside of the tissue (e.g., a healthy tissue near the tumor, etc.) and present at any given time in the tumor microenvironment.

In particularly contemplated embodiments, the inventors contemplate that the IL-8 mediated effect, especially in the tumor microenvironment of a patient, includes, but is not limited to, triggering transmigration of a cell, triggering epithelial-mesenchymal transition of the tumor, triggering metastasis of the tumor, increasing immune suppression in the tumor microenvironment, stimulation of MDSC development, and triggering Th2-biased immune response in the tumor microenvironment. Thus, and without wishing to be bound to specific theory, the inventors contemplate that reducing the quantity of IL-8 from the tumor microenvironment by trapping free IL-8 (IL-8 not bound to IL-8 receptor) reduces the IL-8 effect or even reverse the IL-8 effect to the tumor cells: reducing epithelial-mesenchymal transition of the tumor, reducing or preventing metastasis of the tumor, reducing Th2-biased immune response or rebalancing Th1- and Th2-mediated immune response, and reducing or preventing immune suppression in the tumor microenvironment. Especially, where excessive or abnormal increase of IL-8 expression (or accumulation) is shown in specific types of cancers (e.g., pancreatic cancer, triple negative breast cancer, glioblastoma, etc.) relative to corresponding healthy tissue, it is expected that binding or entrapment of IL-8 may change the prognosis of those types of cancers more effectively.

With respect to dose and schedule of the pharmaceutical composition administration to a patient, it is contemplated that the dose and/or schedule may vary depending on the type of peptides (e.g., scFv, an antibody, an antibody fragment, combination of any two of those, combination of all, etc.), type and prognosis of disease (e.g., tumor type, size, location), health status of the patient (e.g., including age, gender, etc.). While it may vary, the dose and schedule may be selected and regulated so that the formulation does not provide any significant toxic effect to the host normal cells, yet sufficient to be reduce IL-8 effect in the tumor microenvironment at least 20%, preferably at least 30%, more preferably at least 40%, most preferably at least 50% within less than 3 hours, 6 hours, 12 hours, 24 hours, 72 hours, or a week.

In some embodiments, the effect of IL-8 and the reduction of IL-8 effect can be measured by quantity of free IL-8 (either 72-mer or 77-mer) in the tissue. In these embodiments, the administration conditions are typically adjusted to have a quantity or concentration of at least one of 72-mer or 77-mer free IL-8 reduced at least 30%, more preferably at least 40%, most preferably at least 50% within less than 3 hours, 6 hours, 12 hours, 24 hours, 72 hours, or a week after administering the pharmaceutical composition. In other embodiments, the effect of IL-8 and the reduction of IL-8 effect can be measured via in vitro or in vivo measurement of biological activities. For example, the dose and treatment schedule for reducing cell migration or metastasis of a tumor can be determined by in vitro cell migration assay by IL-8. In this example, the administration conditions are typically adjusted to reduce the number of cells migrating from the original position or to reduce the distance of migration of migrating cells at least 20%, preferably at least 30%, more preferably at least 40%, most preferably at least 50% within 1 hour, 3 hours, 6 hours, 12 hours after treatment with the pharmaceutical composition (or scFv, antibody or fragment thereof without pharmaceutically acceptable carrier). For other example, the dose and treatment schedule for reducing immune suppression by myeloid-derived suppressor cells can be determined by measuring the accumulation or presence of myeloid-derived suppressor cells in the tumor. Thus, in this example, the administration conditions are typically adjusted to reduce the number of myeloid-derived suppressor cells (in the entire tumor tissue or per $cm^2$ of tumor tissue) at least 20%, preferably at least 30%, more preferably at least 40%, most preferably at least 50% within 3 hours, 6 hours, 12 hours, 24 hours, 72 hours, or a week after administering the pharmaceutical composition.

In still other embodiments, the effect of IL-8 and the reduction of IL-8 effect can be measured via measuring quantity or concentration of local cytokine molecules. For example, the dose and treatment schedule for reducing Th-2 mediated immune response can be determined by measuring the quantity or concentration of at least one of IL-4, IL-5, IL-6, IL-9, IL-19, and IL-13 in the tumor microenvironment. Thus, in this example, the administration conditions are typically adjusted to reduce the quantity or concentration of at least one of IL-4, IL-5, IL-6, IL-9, IL-19, and IL-13 for at least 20%, preferably at least 30%, more preferably at least 40%, most preferably at least 50% within 3 hours, 6 hours, 12 hours, 24 hours, 72 hours, or a week after administering the pharmaceutical composition.

In still other embodiments, the effect of IL-8 and the reduction of IL-8 effect can be measured via measuring, in vitro or in vivo, expression level of one or more cellular markers. For example, the dose and treatment schedule for reducing epithelial-mesenchymal transition of tumor cells can be determined by measuring expression of E-cadherin epithelial marker and N-cadherin mesenchymal marker in the tumor cells. Thus, the administration conditions are typically adjusted to reduce the expression level of N-cadherin mesenchymal marker at least 20%, preferably at least 30%, more preferably at least 40%, most preferably at least 50% within 3 hours, 6 hours, 12 hours, 24 hours, 72 hours, or a week after administering the pharmaceutical composition, or increase the expression level (compared to IL-8 treatment only) of E-cadherin epithelial marker at least 20%, preferably at least 30%, more preferably at least 40%, most preferably at least 50% within 3 hours, 6 hours, 12 hours, 24 hours, 72 hours, or a week after administering the pharmaceutical composition. It is also contemplated that the ratio between N-cadherin and E-cadherin expression in the tumor cells can be also be an indicator of the effect of IL-8 and the reduction of IL-8 effect. In this example, the administration conditions are typically adjusted to increase the ratio of E-cadherin:N-cadherin expression levels at least 20%, preferably at least 30%, more preferably at least 40%, most preferably at least 50% within 3 hours, 6 hours, 12 hours, 24 hours, 72 hours, or a week after administering the pharmaceutical composition.

Viewed from a different perspective, the reduction of IL-8 mediated effects in vivo can also be observed by physiological phenomena. For example, reduced IL-8 concentration can be observed via reduction or abolishment of EMT (epithelial-mesenchymal transition) of tumor cells and reduction in the associated signaling pathways. Similarly, reduced IL-8 concentrations in a patient and especially in a tumor microenvironment will reduce the stemness of tumor cells as can be readily observed by appropriate stem cell markers. In yet other physiological effects of IL-8 reduction, development of MDSC is typically reduced, as well as a Th2 biased immune response in T cells within the tumor (thus shifting the Th1/Th2 balance towards a Th1 type response.

Additionally, the inventors contemplate that the effect of scFv, antibody or fragment thereof against IL-8 to reduce epithelial-mesenchymal transition of tumor cells in specific type of cancer can be boosted by co-administration of one or more cancer medications. The cancer medications includes, but not limited to, Fulvestrant, Aldoxorubicin, Docetaxel, a tumor necrosis treatment agent (e.g., $^{131}$I-chTNT-3, etc.), Avelumab (a human monoclonal IgG1 antibody that blocks interaction between PD-L1 and its receptor), Brachyury-targeting vaccine (e.g., ETBX-051 (Ad5 [E1-, E2b-]-Brachyury)), Her2-targeting vaccine (e.g., ETBX-021, etc.), MUC-1-targeting vaccine (e.g., ETBX-061 (Ad5 [E1-, E2b-]-MUC1)), and yeast vaccines (e.g., GI-4000 (GI-4014, GI-4015, GI-4016, GI-4020), GI-6207, GI-6301). Details of these cancer medications are described in PCT/US17/40297, which is incorporated herein as a reference in its entirety.

In some embodiments, the inventors contemplate that the effect of scFv, antibody or fragment thereof against IL-8 can be boosted with co-administration of one or more checkpoint inhibitors. With respect to a protein that interferes with or down-regulates checkpoint inhibition, it is contemplated any suitable peptide ligands that bind to a checkpoint receptor are contemplated. Most typically, binding will inhibit or at least reduce signaling via the receptor, and particularly contemplated receptors include CTLA-4 (especially for $CD8^+$ cells), PD-1 (especially for $CD4^+$ cells), TIM1 receptor, 2B4, and CD160. For example, suitable peptide binders can include antibody fragments and especially scFv, but also small molecule peptide ligands (e.g., isolated via RNA display or phage panning) that specifically bind to the receptors. Once more, it should be appreciated that expression of the peptide molecules will preferably be coordinated such that the neoepitopes or polytope are expressed contemporaneously with one or more of the peptide ligands. Thus, it is typically contemplated that the peptide ligands are produced from a single transcript (which may or may not include the sequence portion encoding the polytope), for example, using an internal ribosome entry site or 2A sequence, or from multiple transcripts.

In other embodiments, the inventors contemplate that one or more immune-stimulatory cytokines can be co-administered to modulate the effect of scFv, antibody or fragment thereof against IL-8. For example, the immune stimulatory cytokines can be selected based on the desired immune response or direction(s) of CD4+ T cell/naïve Th cell polarization. For example, in an embodiment where polarization of Treg cells from naïve CD4+ T cells is desired, the immune stimulatory cytokine may be selected to include IL-2 and TGF-β. In another embodiment where polarization of Th17 cells from naïve CD4+ T cells is desired, the immune stimulatory cytokine may be selected to include IL-6 and TGF-β. Likewise, the immune stimulatory cytokine for Th1 cell polarization may include IL-12 and IFN-γ, and the immune stimulatory cytokine for Th2 cell polarization may include IL-4. Additionally, the immune stimulatory cytokine for Tfh cell (follicular helper T cell) polarization may include IL-6 and IL-12, and the immune stimulatory cytokine for CD4+ cytotoxic T cell polarization may include IL-2.

The inventors further contemplate that the scFv, antibody or fragment thereof against IL-8 can be co-treated (or co-administered) to the cancer patient with activated or modified immune cells that can provide the scFv, antibody or fragment thereof against IL-8, better access to the tumor microenvironment by reducing the effect of immune suppression by tumor cells or myeloid-derived suppressor cells in the tumor microenvironment so that the effect of the scFv, antibody or fragment thereof against IL-8 can be maximized. For example, the activated or modified immune cells may include naïve NKT cells or genetically modified NKT cells expressing a chimeric protein or T cell receptor complex to induce NKT cell immune response, and/or to change the microenvironment of the tumor (e.g., by suppressing activity of myeloid-derived suppressor cells). Preferably, the chimeric protein or T cell receptor of genetically modified NKT cells binds a tumor (neo)epitope, a tumor associated antigen, or a self-lipid presented on the tumor cells. For other example, the modified immune cells may include NKT cells genetically modified to express at least one of CD40L and Fas-L, preferably on their cell surfaces. Details of genetically modified and/or naïve, activated NKT cells to reduce immune suppression in the cancer microenvironment are described in Int. App. No. PCT/US18/53506 (and its corresponding published US national phase application), which is incorporated herein in its entirety. Likewise, the activated or modified immune cells may include naïve T cells or genetically modified T cells expressing a chimeric protein or T cell receptor complex to induce T cell immune response, and/or to change the microenvironment of the tumor (e.g., by suppressing activity of myeloid-derived suppressor cells). Preferably, the chimeric protein or T cell receptor of genetically modified NKT cells binds a tumor (neo)epitope, a tumor associated antigen, or a self-lipid presented on the tumor cells.

For still other example, the activated or modified immune cells may include genetically modified NK cells expressing killer activating receptor (KAR) targeting soluble NK cell receptor ligands (e.g., NKG2D, Nkp-30, Nkp-44, Nkp-46, etc), which prevents effective NK cell activity by acting as a decoy ligand to the NK cell receptors. Details of genetically modified NK cells with KAR are described in U.S. Prov. App. No. 62/569,503, which is incorporated herein in its entirety.

In some embodiments, one or more above cancer medications, immune stimulatory cytokines, checkpoint inhibitors, and/or naïve or genetically modified NK cells or NKT cells can be formulated in the same pharmaceutical composition with scFv, antibody or fragment thereof, against IL-8. In other embodiments, the cancer medication can formulated in a separate pharmaceutical composition that can be provided together with the pharmaceutical composition of scFv, antibody or fragment thereof, or administered before the patient is administered with the pharmaceutical composition of scFv, antibody or fragment thereof.

Therefore, it should be appreciated that the IL-8 binding molecules presented herein may form of a treatment regimen that includes administration of the IL-8 binding molecules presented herein. For example, it is contemplated that treatment of a cancer patient (e.g., pancreatic cancer, triple negative breast cancer, glioblastoma) may be performed in an orchestrated manner in which a first drug (e.g., fulvestrant) is administered to reverse EMT to MET (mesenchymal to epithelial transition) and in which a second drug (e.g., aldoxorubicin) is administered to specifically target the hypoxic tumor microenvironment. Such treatment regimen is thought to reduce immune suppressive environment and increase cell stress in a tumor cell, resulting in an increased immunogenicity of the tumor cells to the immune system. Moreover, the treatment may also include tumor necrosis targeting antibodies that will 'label' necrotic tumor cells and so increase susceptibility to attack by NK cells and/or cytotoxic T cells. The IL-8 binding molecules presented herein are co-administered to further suppress IL-8 mediated immune suppressive effects as noted above. Additionally, upon reduction of immune suppressive conditions as noted above, the patient may then receive immune therapy, typically using recombinant vaccines that express one or more of brachyury, tumor or cancer associated antigens, and/or patient- and tumor specific neoantigens. Thus, cancer treatment will include at least two (or at least three, or at least four) of the following: A tumor necrosis targeting drug, a drug that targets the hypoxic tumor microenvironment, a drug that reverses EMT to MET, a vaccine component (recombinant virus, yeast, and/or bacteria), and IL-8 binding molecules as presented herein.

EXAMPLES

The inventors generated scFv molecules (43-12) using nucleic acid sequences of SEQ ID No. 10 (43-12 $V_H$) encoding $V_H$ segment and SEQ ID No. 25 (43-12 $V_L$) encoding $V_L$ segment, and determined the binding affinities to IL-8 (72-mer and 77-mer) and cross-reactivities to other orthologs or paralogs of IL-8. As shown in FIG. 1A, the 43-12 scFv molecule exhibits strong affinity to both 72-mer and 77-mer of IL-8 (with KD 385 pM and 440 pM), and very little cross reactivities, if any, with paralogs (hCXCL1, hCXCL2, hCXCL7) or an ortholog (mCXCL1).

Figure 1B:
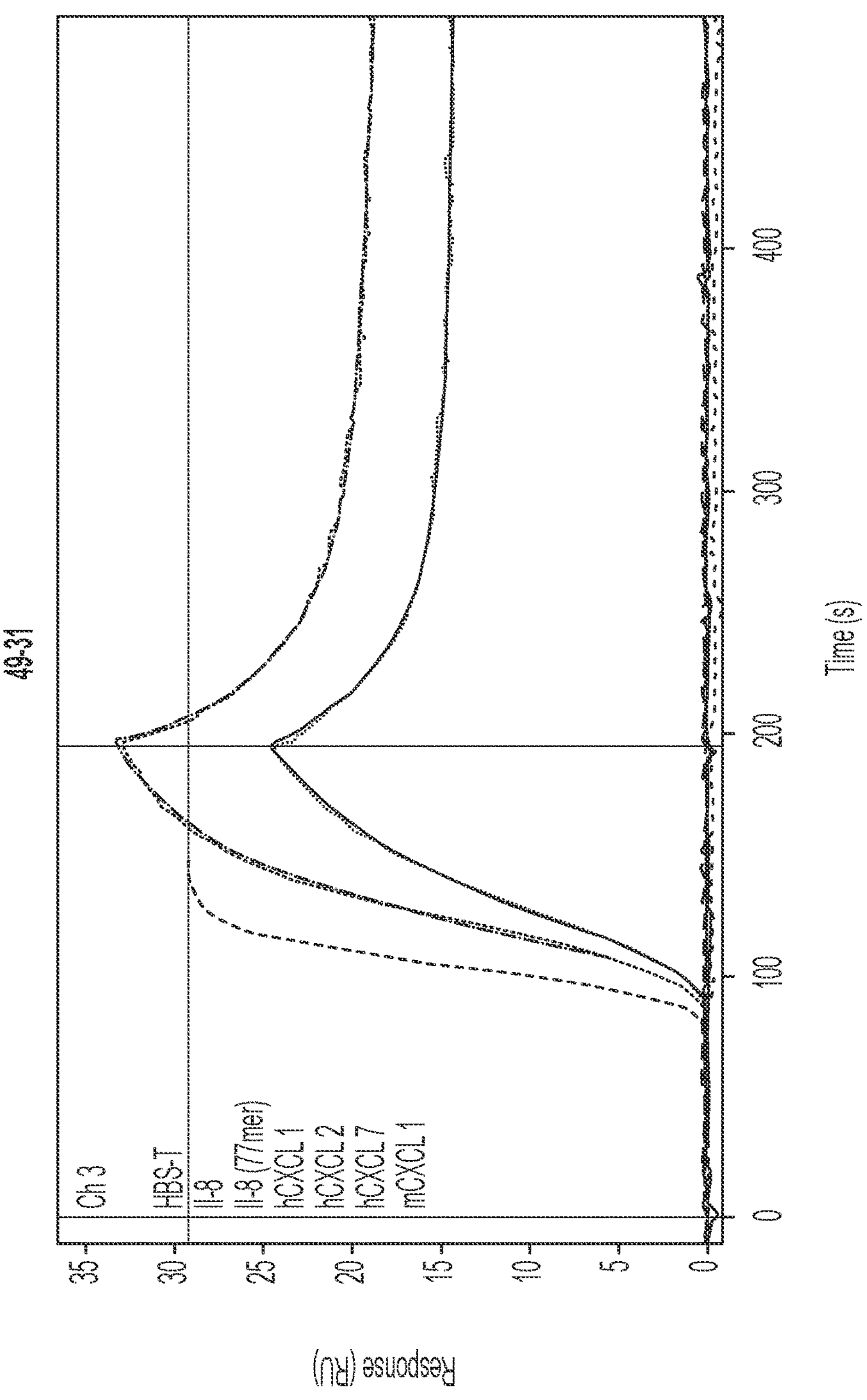
FIG. 1B shows a graph of binding kinetics between one of scFv peptide (49-31) with IL-8 or IL-8 orthologs or paralogs.

The inventors also generated scFv molecules (49-31) using nucleic acid sequences of SEQ ID No. 1 (49-31 $V_H$) encoding $V_H$ segment and SEQ ID No. 16 (49-31 $V_L$) encoding $V_L$ segment, and determined the binding affinities to IL-8 (72-mer and 77-mer) and cross-reactivities to other orthologs or paralogs of IL-8. As shown in FIG. 1B, the 49-31 scFv molecule exhibits strong affinity to both 72-mer and 77-mer of IL-8 (with KD 147 pM and 120 pM), and very little cross reactivities, if any, with paralogs (hCXCL1, hCXCL2, hCXCL7) or an ortholog (mCXCL1).

Figure 2A:
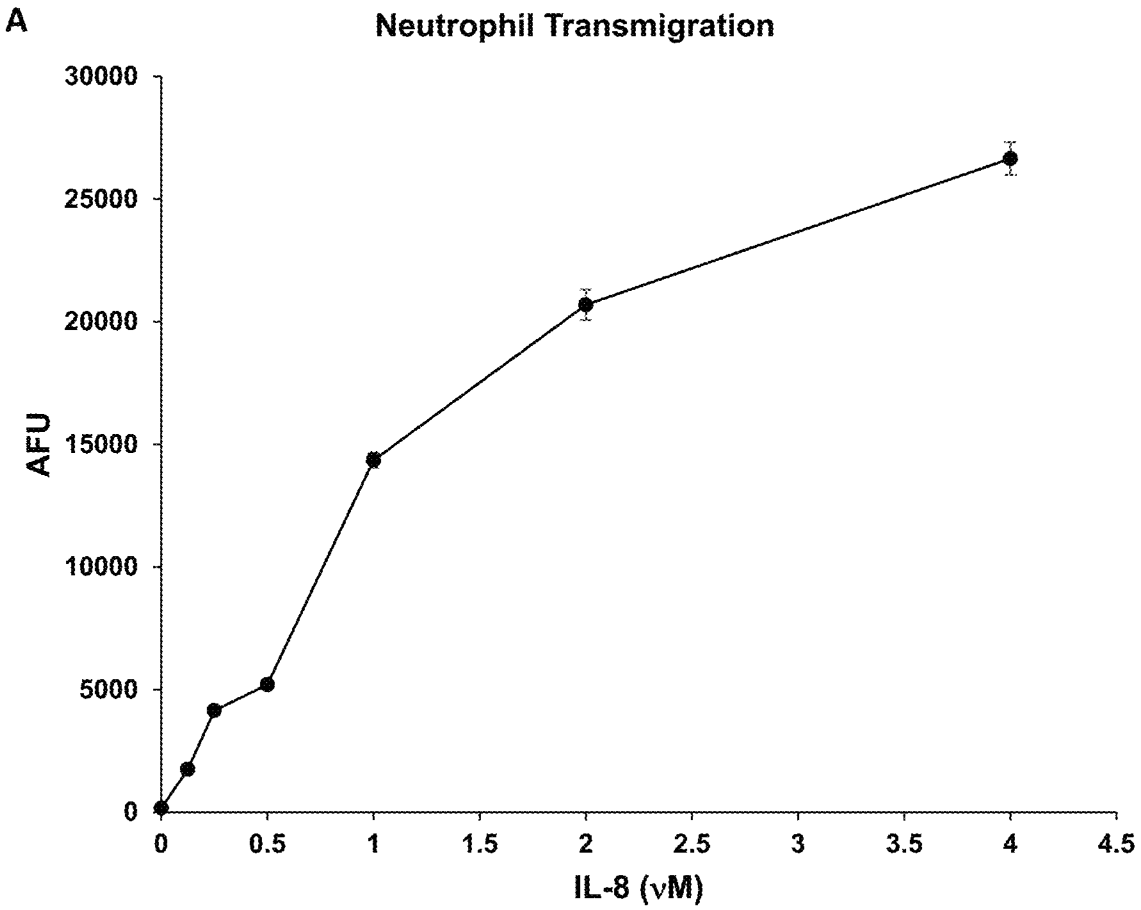
FIGS. 2A-D show graphs of neutrophil transmigration upon IL-8 treatment (2A, 2C) and with scFv peptide co-treatment with IL-8 (2B, 2D).
Figure 2B:
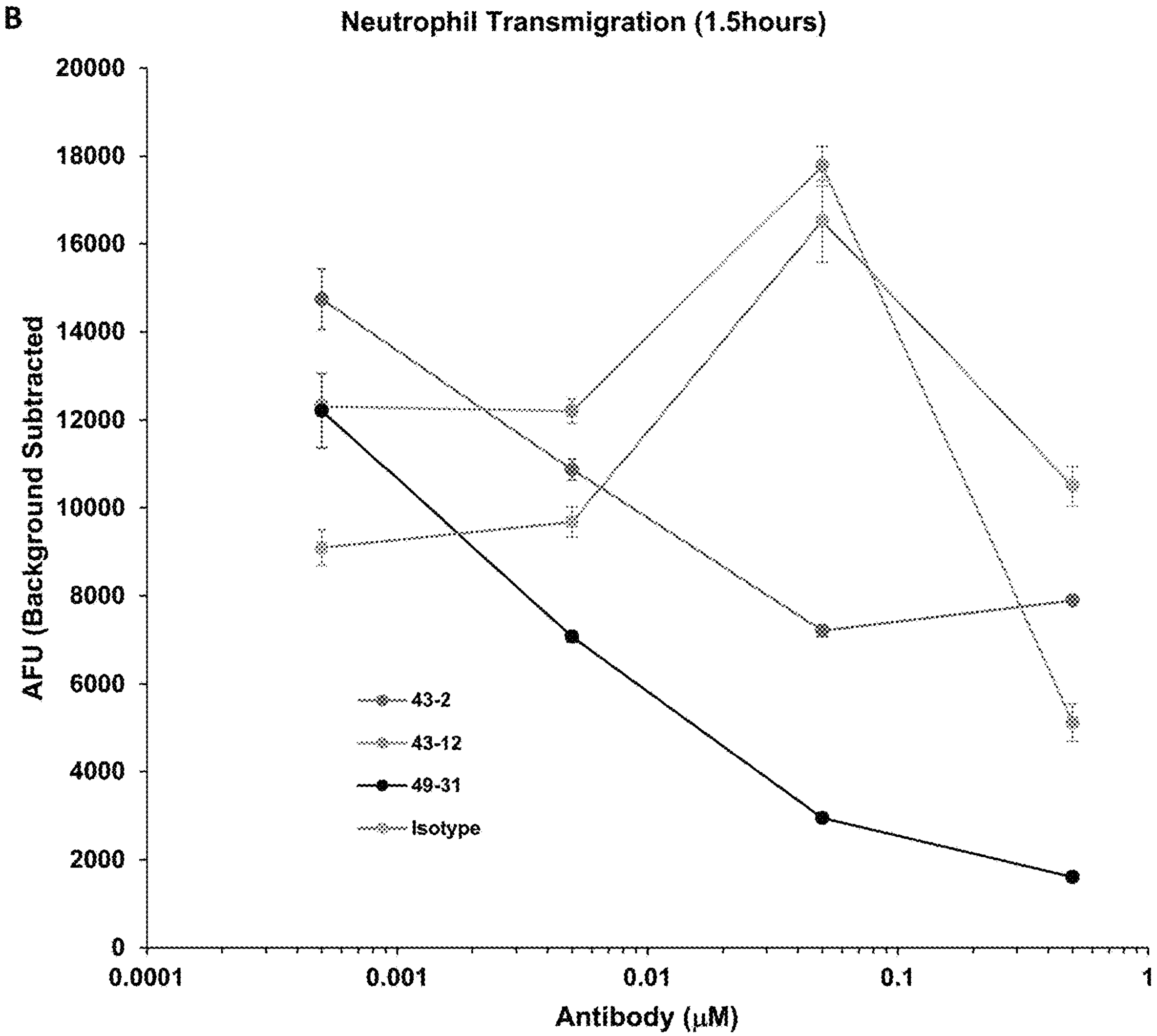
Figure 2C:
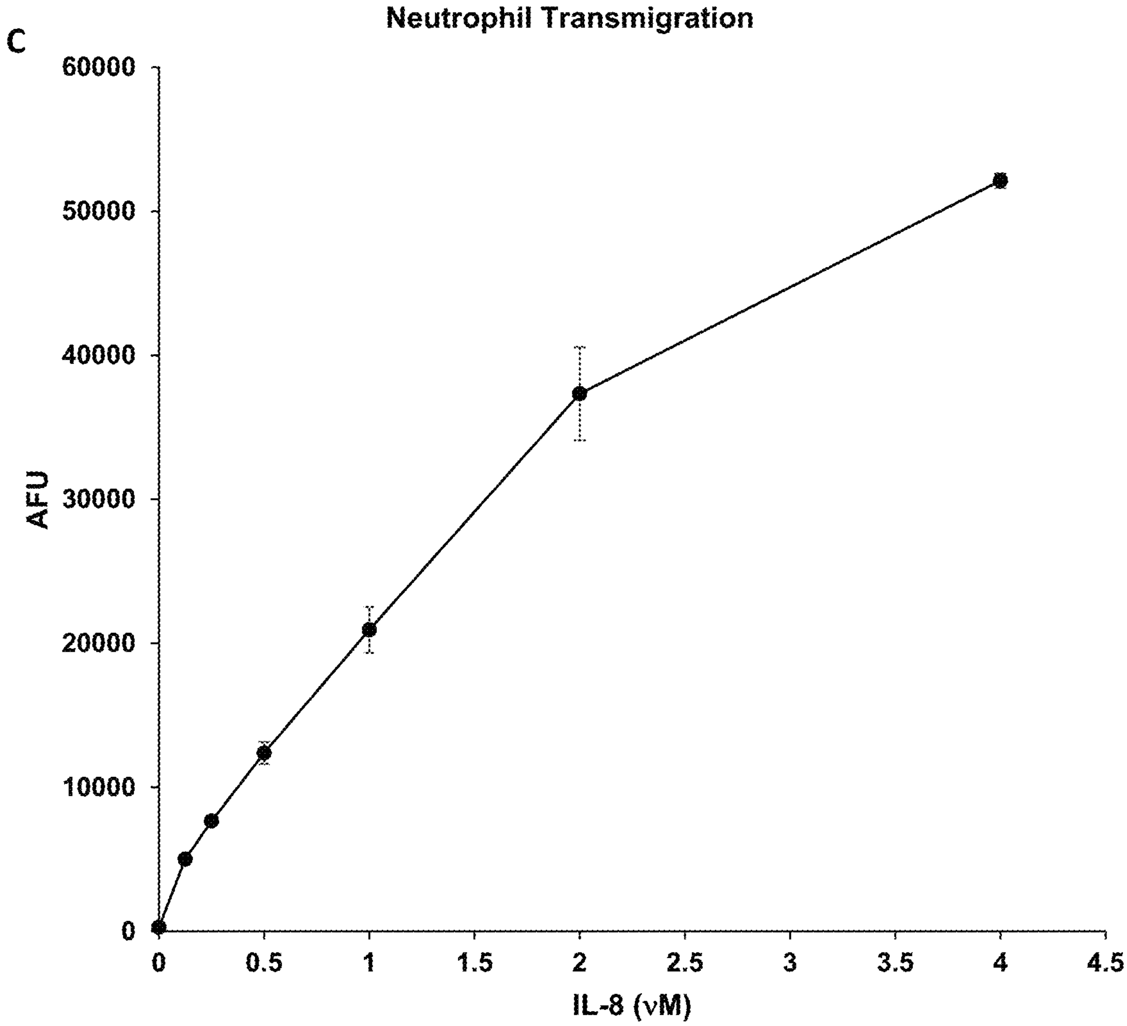
Figure 2D:
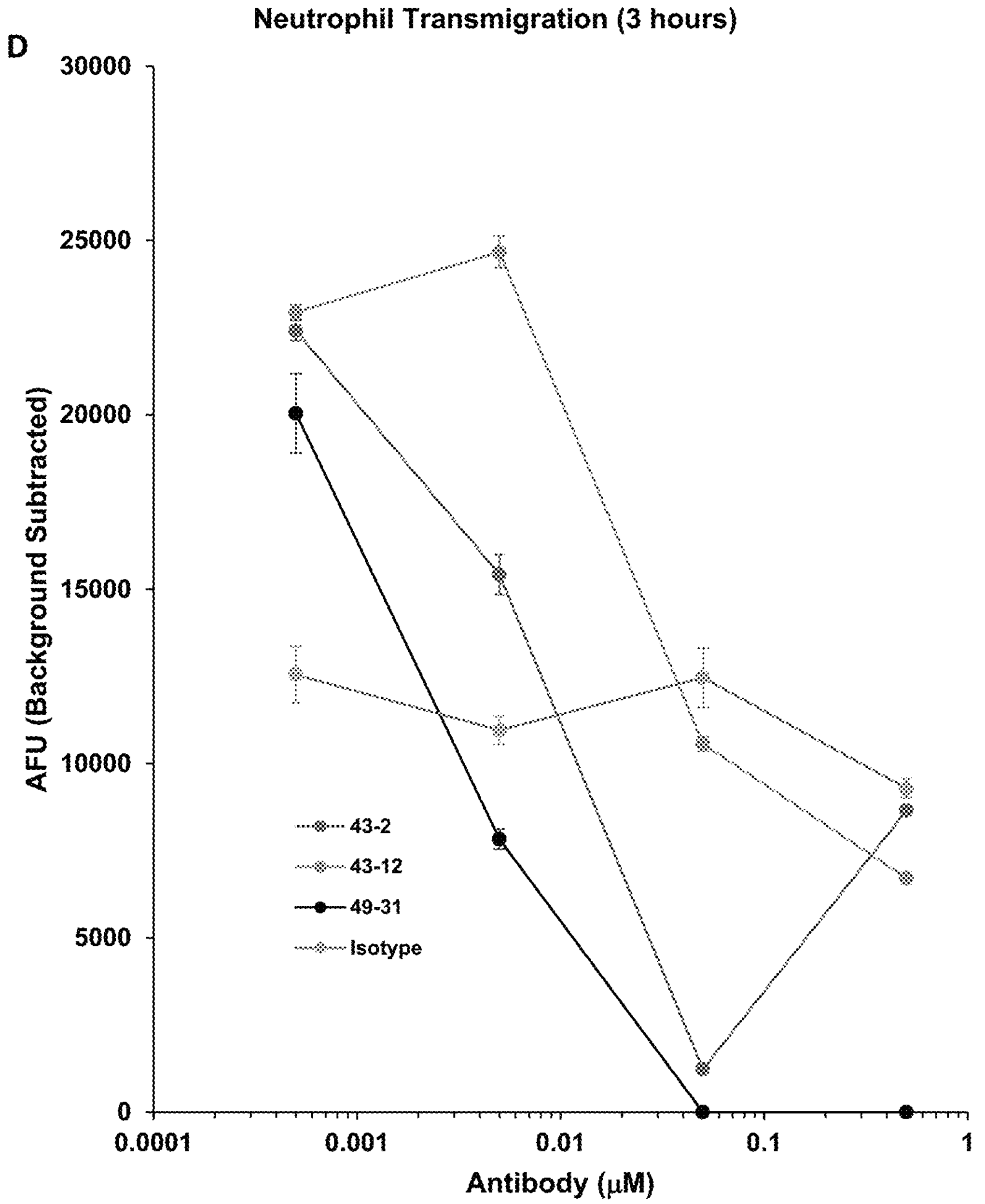

Next, the inventors tested so-generated scFv molecules (43-2, 43-12, 49-31, etc. all also shown in Table 3) to determine their neutralizing effect of IL-8. In one exemplary set of experiments, primary human neutrophils were isolated from blood to assess the ability of the scFv molecules (here: 43-2, 43-12, 49-31) to neutralize IL-8 mediated neutrophil chemotaxis. In a 3 mM pore size transwell plate, 1 nM of recombinant human IL-8 was incubated with a titration of antibodies as indicated in the left panel, and 50,000 calcein-AM labeled neutrophils were added into the top chamber for 1.5 and 3 hours. Transmigration of neutrophils was assessed by assaying for total fluorescence in the bottom chamber and background subtracted against blank media only wells. FIG. 2, panels A-D show graphs representing neutrophil migration in vitro upon treatment of IL-8 alone (FIG. 2A, FIG. 2C) and IL-8 and one of scFv molecules (43-2, 43-12, 49-31) for 1.5 hours (FIG. 2B) or for 3 hours (FIG. 2D). As shown in FIGS. 2B and 2D, all scFv molecules (43-2, 43-12, 49-31) could reduce the transmigration of neutrophils 30-70% with less than 1 uM concentration in both 1.5 hours and 3 hours, indicating that all scFv molecules (43-2, 43-12, 49-31) are effective in mitigating the effect of IL-8 by entrapping free IL-8 in the serum (or media).

Figure 3:
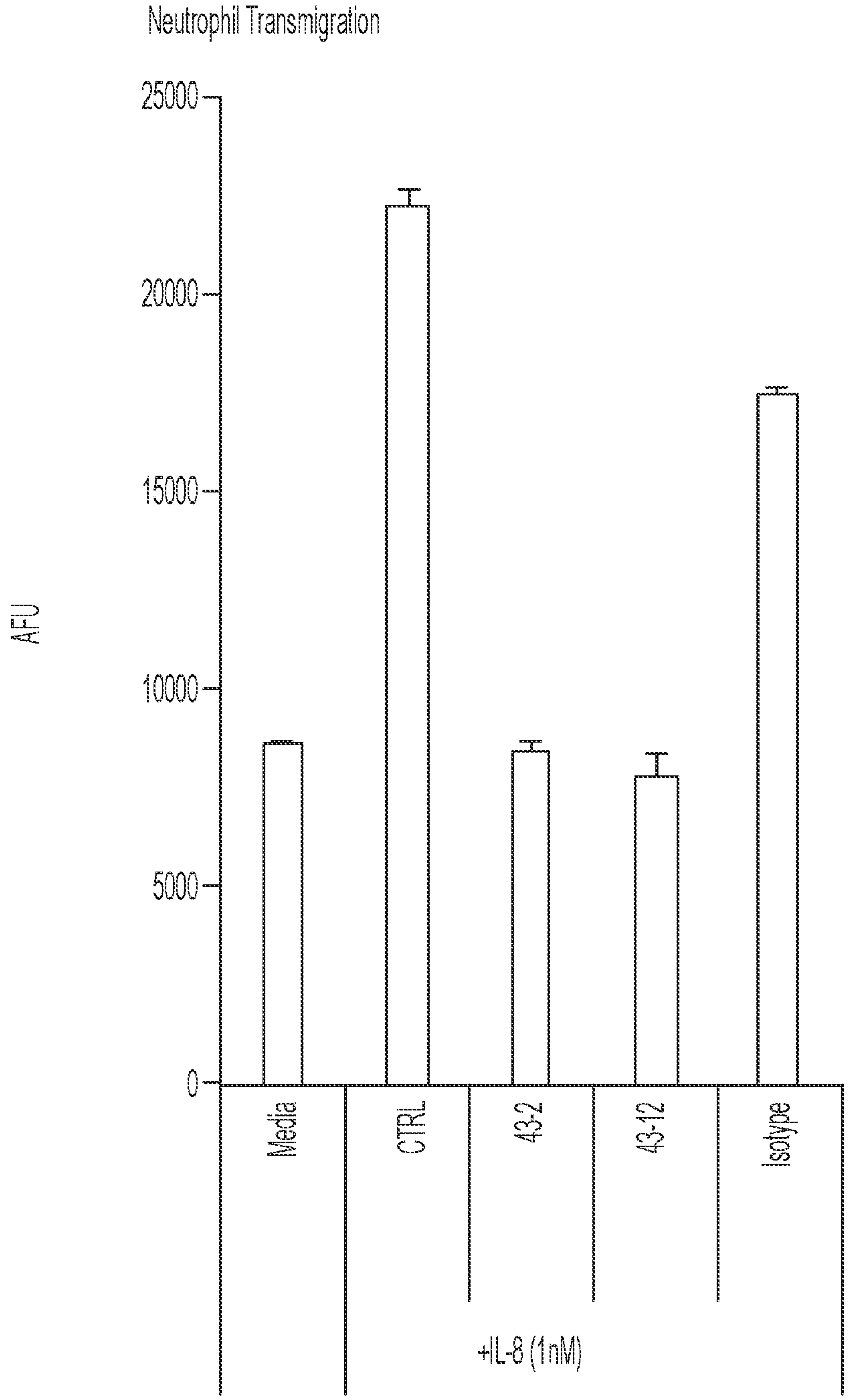
FIG. 3 shows a graph of neutrophil transmigration upon IL-8 treatment (CTRL) and with scFv peptide co-treatment with IL-8 (43-2, 43-12).

FIG. 3 shows a graph indicating the neutrophil transmigration upon treatment of IL-8 alone (CTRL) and IL-8 and one of scFv molecules (43-2, 43-12) in 1 nM concentration. Both scFv molecules (43-2, 43-12) could completely reverse the effect of IL-8 such that the levels of neutrophil migration with scFv molecules (43-2, 43-12) treatment are similar or almost identical to media alone, while IL-8 treatment alone could increase the neutrophil migration almost three times compared to the media alone.

Figure 4A:
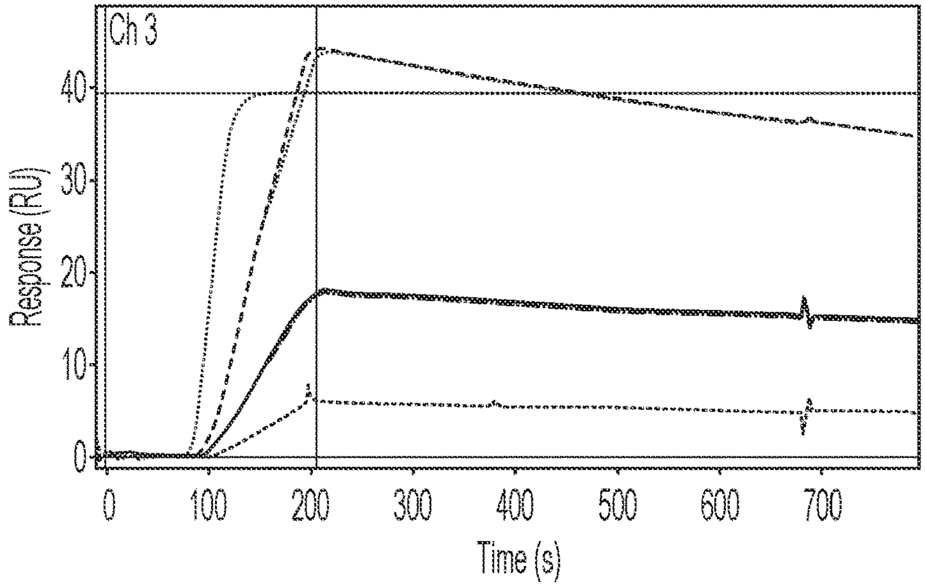
FIGS. 4A-C show graphs of binding kinetics between one of scFv peptide (43-12) with IL-8 under specific pH conditions (4A), and binding kinetics for selected affinity maturated variant scFv peptides (43-12a and 43-12b) under specific pH conditions.
Figure 4A:
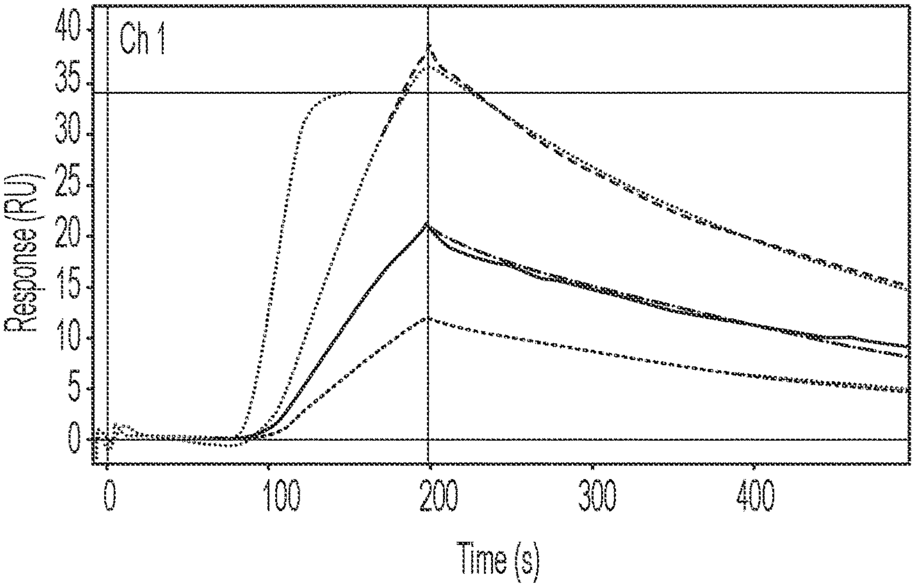
Figure 4B:
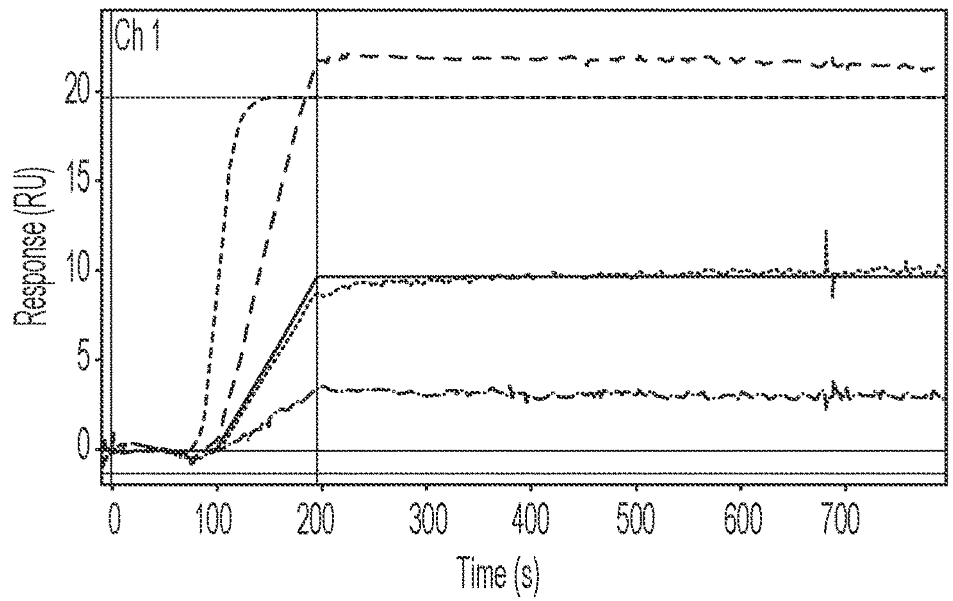
Figure 4B:
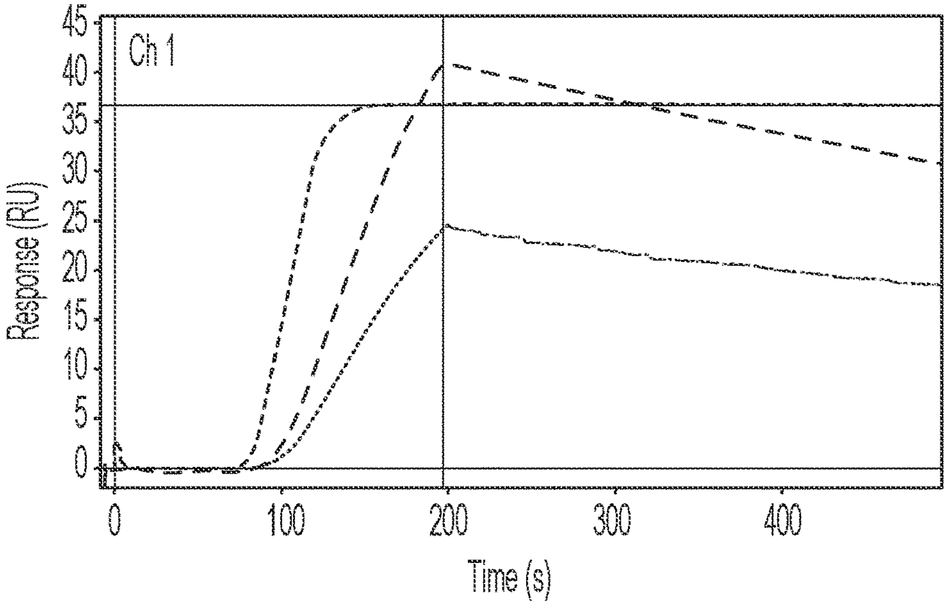
Figure 4C:
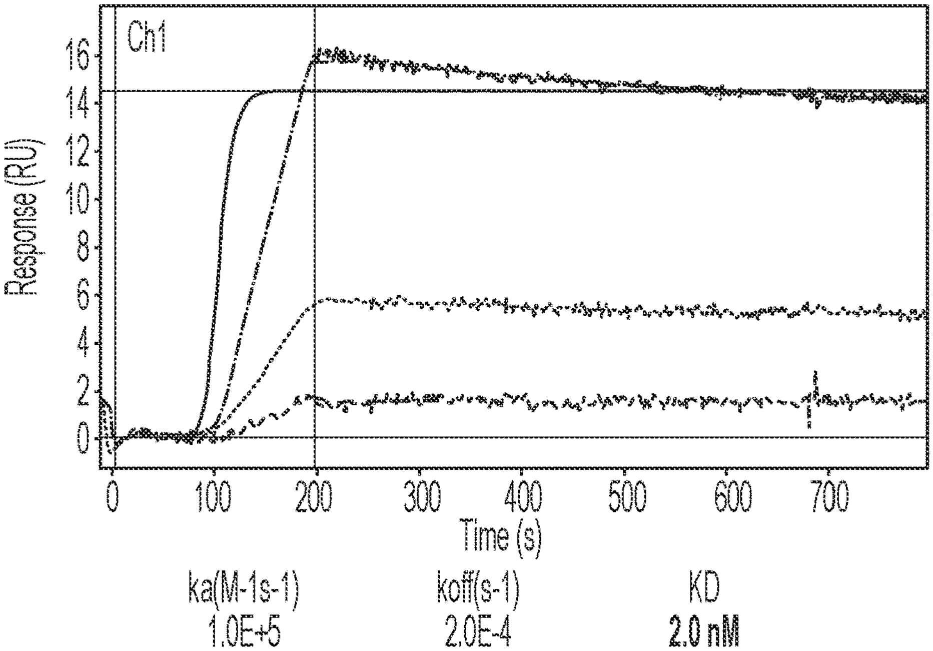
Figure 4C:
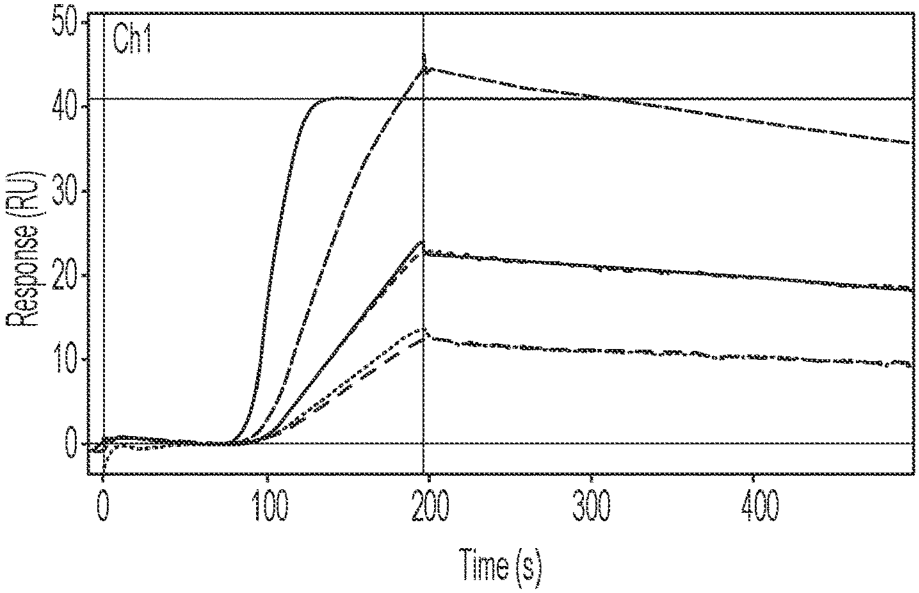

In yet another set of experiments, the inventors used affinity maturation (here: random mutagenesis of CDR regions in VH and VL chains and mRNA display selection) of one previously identified IL-8 binder (here: 43-12, sequence in Table 1), and SPR analysis was performed on selected mutant forms using two different pH conditions, pH 7.4 and pH 6.0. As can be seen from the results in FIGS. 4A-C (with FIG. 4A depicting results for the parent scFv 43-12), both derivative mutant forms had improved binding over the parent scFv. Specifically, FIG. 4B shows exemplary results for 43-12a (sequences shown in Table 1) and FIG. 4C shows exemplary results for 43-12b (sequences shown in Table 1).

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A method of reducing epithelial-mesenchymal transition (EMT) in a patient having a tumor, the method comprising:

a. providing a pharmaceutical composition comprising a recombinant antibody, single chain variable fragment (scFv) peptide, or fusion protein comprising the antibody or scFv, wherein the antibody, scFv peptide, or fusion protein binds to IL-8;

b. wherein the antibody, scFv peptide, or fusion protein has a VH segment and a VL segment respectively consisting of SEQ ID NO:8 and SEQ ID NO:23, SEQ ID NO: 10 and SEQ ID NO:25, SEQ ID NO:31 and SEQ ID NO:33, or SEQ ID NO: 32 and SEQ ID NO:34; and c. administering the pharmaceutical composition to the patient.

2. The method of claim 1, wherein the recombinant antibody is coupled to a protein having IL-15 activity, a protein having IL-15 receptor alpha activity, or a T×M fusion protein comprised thereof.

3. The method of claim 1, further comprising a step of administering at least one of the following: Fulvestrant, Aldoxorubicin, Docetaxel, a tumor necrosis targeting agent (TNT), and a tumor vaccine.

4. The method of claim 1, wherein the reduction in EMT is determined by measuring tumor expression of at least one marker selected from the group consisting of E-Cadherin, N-cadherin, and the ratio of E-Cadherin to N-Cadherin.

5. The method of claim 1, further comprising co-administering to the patient an immune-stimulatory cytokine selected from a group consisting of IL-2, IL-12, IL-15, an IL-15 super agonist ALT803), IL-21, IPS1, and LMP1.

6. The method of claim 1, wherein the pharmaceutical composition is administered in a dose and a schedule effective to reduce free IL-8 in the tumor in the patient by at least 30%.

7. The method of claim 1, wherein the pharmaceutical composition is administered in a dose and a schedule effective to reduce EMT of the tumor in the patient by at least 30%.

8. The method of claim 1, wherein the pharmaceutical composition is administered in a dose and a schedule effective to reduce the number of myeloid-derived suppressor cells in the tumor in the patient by at least 30%.

9. The method of claim 1, wherein the tumor is at least one of the following: pancreatic cancer, triple negative breast cancer, glioblastoma.

10. The method of claim 1, further comprising co-administering to the patient a checkpoint inhibitor, wild type or genetically modified natural killer cell, or a tumor vaccine.

11. A method of reducing immune suppression in a patient having a tumor, the method comprising:

a. providing a pharmaceutical composition comprising a recombinant antibody, single chain variable fragment (scFv) peptide, or fusion protein comprising the antibody or scFv, wherein the antibody, scFv peptide, or fusion protein binds to IL-8;

b. wherein the antibody, scFv peptide, or fusion protein has a VH segment and a VL segment respectively consisting of SEQ ID NO:8 and SEQ ID NO:23, SEQ ID NO: 10 and SEQ ID NO:25, SEQ ID NO:31 and SEQ ID NO:33, or SEQ ID NO: 32 and SEQ ID NO:34; and c. administering the pharmaceutical composition to the patient.

12. The method of claim 11, wherein the recombinant antibody is coupled to a protein having IL-15 activity, a protein having IL-15 receptor alpha activity, or a T×M fusion protein comprised thereof.

13. The method of claim 11, further comprising a step of administering at least one of the following: Fulvestrant, Aldoxorubicin, Docetaxel, a tumor necrosis targeting agent (TNT), and a tumor vaccine.

14. The method of claim 11, wherein the reduction in immune suppression is mediated by reduced recruitment of Myeloid-Derived Suppressor Cells the the tumor microenvironment.

15. The method of claim 11, further comprising co-administering to the patient an immune-stimulatory cytokine selected from a group consisting of IL-2, IL-12, IL-15, an IL-15 super agonist ALT803), IL-21, IPS1, and LMP1.

16. The method of claim 11, wherein the pharmaceutical composition is administered in a dose and a schedule effective to reduce free IL-8 in the tumor in the patient by at least 30%.

17. The method of claim 11, wherein the pharmaceutical composition is administered in a dose and a schedule effective to reduce at least one of IL-4, IL-5, IL-6, IL-9, IL-19, and IL-13 in the tumor microenvironment by at least 30%.

18. The method of claim 11, wherein the pharmaceutical composition is administered in a dose and a schedule effective to reduce the number of myeloid-derived suppressor cells in the tumor in the patient by at least 30%.

19. The method of claim 11, wherein the tumor is at least one of the following: pancreatic cancer, triple negative breast cancer, glioblastoma.

20. The method of claim 11, further comprising co-administering to the patient a checkpoint inhibitor, or a tumor vaccine.

* * * * *

SEQUENCE LISTING

```
Sequence total quantity: 34
SEQ ID NO: 1            moltype = AA  length = 122
FEATURE                 Location/Qualifiers
REGION                  1..122
                        note = mRNA display generated artificial sequence 49-31 VH
source                  1..122
                        mol_type = protein
                        organism = synthetic construct
SEQUENCE: 1
EVQLVESGGG LVQPGGSLRL SCAASGFTFS SYYMHWVRQA PGKGLEWVSA ISGGGSSTYY  60
ADSVKGRFTI SRDNSKNTLY LQMNSLRAED TAVYYCARDL RIFEGRDAGF DVWGQGTLVT  120
VS                                                                122

SEQ ID NO: 2            moltype = AA  length = 123
FEATURE                 Location/Qualifiers
REGION                  1..123
                        note = mRNA display generated artificial sequence 49-22 VH
source                  1..123
                        mol_type = protein
                        organism = synthetic construct
SEQUENCE: 2
EVQLVESGGG LVQPGGSLRL SCAASGFTFT SYAMHWVRQA PGKGLEWVSA ISGSGGSTYY  60
ADSVKGRFTI SRDNSKNTLY LQMNSLRAED TAVYYCARDL DMFVPFWPAF DVWGQGTLVT  120
VSS                                                               123

SEQ ID NO: 3            moltype = AA  length = 121
FEATURE                 Location/Qualifiers
REGION                  1..121
                        note = mRNA display generated artificial sequence 49-7 VH
source                  1..121
                        mol_type = protein
                        organism = synthetic construct
SEQUENCE: 3
EVQLVESGGG LVQPGGSLRL SCAASGFTFS SYAMHWVRQA PGKGLEWVSA ISNSGASTYY  60
ADSVKGRFTI SRDNSKNTLY LQMNSLRAEN TAVYYCARDL MRWWIDGFDV WGQGTLVTVS  120
S                                                                 121

SEQ ID NO: 4            moltype = AA  length = 122
FEATURE                 Location/Qualifiers
REGION                  1..122
                        note = mRNA display generated artificial sequence 49-32 VH
source                  1..122
                        mol_type = protein
                        organism = synthetic construct
SEQUENCE: 4
EVQLVESGGG LVQPGGSLRL SCAASGFTFS SYAMHWVRQA PGKGLEWVSA IYGNGGSTYY  60
ADSVKGRFTI SRDNSKNTLY LQMNSLRAED TAVYYCARDL YTIEPREAFD VWGQGTLVTV  120
SS                                                                122

SEQ ID NO: 5            moltype = AA  length = 122
FEATURE                 Location/Qualifiers
REGION                  1..122
                        note = mRNA display generated artificial sequence 49-34 VH
source                  1..122
                        mol_type = protein
                        organism = synthetic construct
SEQUENCE: 5
```

-continued

```
EVQLVESGGG LVQPGGSLRL SCAASGFTLG SYAMHWVRQA PGKGLEWVSA ISGSGGSTYY  60
ADSVKGRFTI SRDNSKNTLY LQMNSLRAED TAVYYCARDR DTVSIEVGFD VWGQGTLVTV  120
SS                                                                122

SEQ ID NO: 6            moltype = AA  length = 120
FEATURE                 Location/Qualifiers
REGION                  1..120
                        note = mRNA display generated artificial sequence 49-18 VH
source                  1..120
                        mol_type = protein
                        organism = synthetic construct
SEQUENCE: 6
EVQLVESGGG LVQPGGSLRL SCAASGFTFS SYAMNWVRQA PGKGLEWVSA ISWSGGNTYY  60
ADSVKGRFTI SRDNSKNTLY LQMNSLRAED TAVYYCARDL YAGYWGFDVW GQGTLVTVSS  120

SEQ ID NO: 7            moltype = AA  length = 125
FEATURE                 Location/Qualifiers
REGION                  1..125
                        note = mRNA display generated artificial sequence 49-3 VH
source                  1..125
                        mol_type = protein
                        organism = synthetic construct
SEQUENCE: 7
EVQLVESGGG LVQPGGSLRL SCAASGFTFS SYAMTWVRQA PGKGLEWVSV ISGSGGSTRY  60
ADSVKGRFTI SRDNSKNTLY LQMNSLRAED TAVYYCARDR KFPYVQFFRN GFDVWGQGTL  120
VTVSS                                                             125

SEQ ID NO: 8            moltype = AA  length = 125
FEATURE                 Location/Qualifiers
REGION                  1..125
                        note = mRNA display generated artificial sequence 43-2 VH
source                  1..125
                        mol_type = protein
                        organism = synthetic construct
SEQUENCE: 8
EVQLVESGGG LVQPGGSLRL SCAASGFTFS SYAMHWVRQA PGKGLEWVSA ISGSGGKTYY  60
ADSVKGRFTI SRDNSKNTLY LQMNSLRAED TAVYYCARDR EAPFYTVYVT GFDVWGQGTL  120
VTVSS                                                             125

SEQ ID NO: 9            moltype = AA  length = 120
FEATURE                 Location/Qualifiers
REGION                  1..120
                        note = mRNA display generated artificial sequence 49-37 VH
source                  1..120
                        mol_type = protein
                        organism = synthetic construct
SEQUENCE: 9
EVQLVESGGG LVQPGGSLRL SCAASGFTFS SYAMNWVRQA PGKGLEWVSA ISYSGGSTYY  60
ADSVKGRFTI SRDNSKNTLY LQMNSLRAED TAVYYCARDL WLGWWGFDVW GQGTLVTVSS  120

SEQ ID NO: 10           moltype = AA  length = 123
FEATURE                 Location/Qualifiers
REGION                  1..123
                        note = mRNA display generated artificial sequence 43-12 VH
source                  1..123
                        mol_type = protein
                        organism = synthetic construct
SEQUENCE: 10
EVQLVESGGG LVQPGGSLRL SCAASGFTFS SYLMHWVRQA PGKGLEWVSA ISGSGGSTYY  60
ADSVKGRFTI SRDNSKNTLY LQMNSLRAED TAVYYCARDR EGWFWHSYGF DVWGQGTLVT  120
VSS                                                               123

SEQ ID NO: 11           moltype = AA  length = 123
FEATURE                 Location/Qualifiers
REGION                  1..123
                        note = mRNA display generated artificial sequence 49-10 VH
source                  1..123
                        mol_type = protein
                        organism = synthetic construct
SEQUENCE: 11
EVQLVESGGG LVQPGGSLRL SCAASGFTFS SYAMNWVRQA PGKGLEWVSA ISGSGGSTYY  60
ADSVKGRFTI SRDNSKNTLY LQMNSLRAED TAVYYCARDL GWLSRLFAGF DVWGQGTLVT  120
VSS                                                               123

SEQ ID NO: 12           moltype = AA  length = 120
FEATURE                 Location/Qualifiers
REGION                  1..120
                        note = mRNA display generated artificial sequence 49-1 VH
source                  1..120
```

-continued

```
                         mol_type = protein
                         organism = synthetic construct
SEQUENCE: 12
EVQLVESGGG LVQPGGSLRL SCAASGFTFS SYWMHWVRQA PGKGLEWVSA ISWSGGSTSY  60
ADSVKGRFTI SRDNSKNTLY LQMNSLRAED TAVYYCARDL TWWVQAFDVW GQGTLVTVSS  120

SEQ ID NO: 13            moltype = AA  length = 121
FEATURE                  Location/Qualifiers
REGION                   1..121
                         note = mRNA display generated artificial sequence 49-6 VH
source                   1..121
                         mol_type = protein
                         organism = synthetic construct
SEQUENCE: 13
EVQLVESGGG LVQPGGSLRL SCAASGFTFS EYAMHWVRQA PGKGLEWVSA IDGNGTSTYY  60
ADSVKGRFTI SRDNSKNTLY LQMNSLRAED TAVYYCARDR DTALETGFDV WGQGTLVTVS  120
S                                                                  121

SEQ ID NO: 14            moltype = AA  length = 119
FEATURE                  Location/Qualifiers
REGION                   1..119
                         note = mRNA display generated artificial sequence 49-12 VH
source                   1..119
                         mol_type = protein
                         organism = synthetic construct
SEQUENCE: 14
EVQLVESGGG LVQPGGSLRL SCAASGFTFS SYYMHWVRQA PGKGLEWVSA ISNSGGSTHY  60
ADSVKGRFTI SRDNSKNTLY LQMNSLRAED TAVYYCARDL WWLPAFDVWG QGTLVTVSS   119

SEQ ID NO: 15            moltype = AA  length = 120
FEATURE                  Location/Qualifiers
REGION                   1..120
                         note = mRNA display generated artificial sequence 49-25 VH
source                   1..120
                         mol_type = protein
                         organism = synthetic construct
SEQUENCE: 15
EVQLVESGGG LVQPGGSLRL SCAASGFTFS SYAMNWVRQA PGKGLEWVSA ISWSGGRTYY  60
ADSVKGRFTI SRDNSKNTLY LQMNSLRAED TAVYYCARDL YDGVWGFDVW GQGTLVTVSS  120

SEQ ID NO: 16            moltype = AA  length = 107
FEATURE                  Location/Qualifiers
REGION                   1..107
                         note = mRNA display generated artificial sequence 49-31 VL
source                   1..107
                         mol_type = protein
                         organism = synthetic construct
SEQUENCE: 16
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ DDDVPWTFGQ GTKVEIK                107

SEQ ID NO: 17            moltype = AA  length = 107
FEATURE                  Location/Qualifiers
REGION                   1..107
                         note = mRNA display generated artificial sequence 49-22 VL
source                   1..107
                         mol_type = protein
                         organism = synthetic construct
SEQUENCE: 17
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ ASDTPLTFGQ GTKVEIK                107

SEQ ID NO: 18            moltype = AA  length = 107
FEATURE                  Location/Qualifiers
REGION                   1..107
                         note = mRNA display generated artificial sequence 49-7 VL
source                   1..107
                         mol_type = protein
                         organism = synthetic construct
SEQUENCE: 18
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ SYDIPLTFGQ GTKVEIK                107

SEQ ID NO: 19            moltype = AA  length = 107
FEATURE                  Location/Qualifiers
REGION                   1..107
                         note = mRNA display generated artificial sequence 49-32 VL
source                   1..107
                         mol_type = protein
```

```
                         organism = synthetic construct
SEQUENCE: 19
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ DYTSPLTFGQ GTKVEIK                107

SEQ ID NO: 20            moltype = AA  length = 107
FEATURE                  Location/Qualifiers
REGION                   1..107
                         note = mRNA display generated artificial sequence 49-34 VL
source                   1..107
                         mol_type = protein
                         organism = synthetic construct
SEQUENCE: 20
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ DSAFPLTFGQ GTKVEIK                107

SEQ ID NO: 21            moltype = AA  length = 107
FEATURE                  Location/Qualifiers
REGION                   1..107
                         note = mRNA display generated artificial sequence 49-18 VL
source                   1..107
                         mol_type = protein
                         organism = synthetic construct
SEQUENCE: 21
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ DYGYPLTFGQ GTKVEIK                107

SEQ ID NO: 22            moltype = AA  length = 107
FEATURE                  Location/Qualifiers
REGION                   1..107
                         note = mRNA display generated artificial sequence 49-3 VL
source                   1..107
                         mol_type = protein
                         organism = synthetic construct
SEQUENCE: 22
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ HTNGPFTFGQ GTKVEIK                107

SEQ ID NO: 23            moltype = AA  length = 107
FEATURE                  Location/Qualifiers
REGION                   1..107
                         note = mRNA display generated artificial sequence 43-2 VL
source                   1..107
                         mol_type = protein
                         organism = synthetic construct
SEQUENCE: 23
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ DADTPLTFGQ GTKVEIK                107

SEQ ID NO: 24            moltype = AA  length = 107
FEATURE                  Location/Qualifiers
REGION                   1..107
                         note = mRNA display generated artificial sequence 49-37 VL
source                   1..107
                         mol_type = protein
                         organism = synthetic construct
SEQUENCE: 24
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YNTIPYTFGQ GTKVEIK                107

SEQ ID NO: 25            moltype = AA  length = 107
FEATURE                  Location/Qualifiers
REGION                   1..107
                         note = mRNA display generated artificial sequence 43-12 VL
source                   1..107
                         mol_type = protein
                         organism = synthetic construct
SEQUENCE: 25
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ VYSGPWTFGQ GTKVEIK                107

SEQ ID NO: 26            moltype = AA  length = 107
FEATURE                  Location/Qualifiers
REGION                   1..107
                         note = mRNA display generated artificial sequence 49-10 VL
source                   1..107
                         mol_type = protein
                         organism = synthetic construct
SEQUENCE: 26
```

```
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ DYGYPLTFGQ GTKVEIK               107

SEQ ID NO: 27          moltype = AA  length = 107
FEATURE                Location/Qualifiers
REGION                 1..107
                       note = mRNA display generated artificial sequence 49-1 VL
source                 1..107
                       mol_type = protein
                       organism = synthetic construct
SEQUENCE: 27
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ VDDSPLTFGQ GTKVEIK               107

SEQ ID NO: 28          moltype = AA  length = 107
FEATURE                Location/Qualifiers
REGION                 1..107
                       note = mRNA display generated artificial sequence 49-6 VL
source                 1..107
                       mol_type = protein
                       organism = synthetic construct
SEQUENCE: 28
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ DNAFPLTFGQ GTKVEIK               107

SEQ ID NO: 29          moltype = AA  length = 107
FEATURE                Location/Qualifiers
REGION                 1..107
                       note = mRNA display generated artificial sequence 49-12 VL
source                 1..107
                       mol_type = protein
                       organism = synthetic construct
SEQUENCE: 29
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ SSGWPFTFGQ GTKVEIK               107

SEQ ID NO: 30          moltype = AA  length = 107
FEATURE                Location/Qualifiers
REGION                 1..107
                       note = mRNA display generated artificial sequence 49-25 VL
source                 1..107
                       mol_type = protein
                       organism = synthetic construct
SEQUENCE: 30
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YSSYPFTFGQ GTKVEIK               107

SEQ ID NO: 31          moltype = AA  length = 123
FEATURE                Location/Qualifiers
REGION                 1..123
                       note = mRNA display generated artificial sequence 43-12a VH
source                 1..123
                       mol_type = protein
                       organism = synthetic construct
SEQUENCE: 31
EVQLVESGGG LVQPGGSLRL SCAASGFTFS SYLMHWVRQA PGKGLEWVSA ISGSGGITYY  60
ADSVKGRFTI SRDNSKNTLY LQMNSLRAED TAVYYCARDR EGWFWHSYGF DVWGQGTLVT  120
VSS                                                               123

SEQ ID NO: 32          moltype = AA  length = 123
FEATURE                Location/Qualifiers
REGION                 1..123
                       note = mRNA display generated artificial sequence 43-12b VH
source                 1..123
                       mol_type = protein
                       organism = synthetic construct
SEQUENCE: 32
EVQLVESGGG LVQPGGSLRL SCAASGFTFS SYLMHWVRQA PGKGLEWVSA ISGSGGITYY  60
ADSVKGRFTI SRDNSKNTLY LQMNSLRAED TAVYYCARDR EGWFWHSYGF DVWGQGTLVT  120
VSS                                                               123

SEQ ID NO: 33          moltype = AA  length = 107
FEATURE                Location/Qualifiers
REGION                 1..107
                       note = mRNA display generated artificial sequence 43-12a VL
source                 1..107
                       mol_type = protein
                       organism = synthetic construct
SEQUENCE: 33
```

-continued

```
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ VYSGPWTFGQ GTKVEIK               107

SEQ ID NO: 34           moltype = AA  length = 107
FEATURE                 Location/Qualifiers
REGION                  1..107
                        note = mRNA display generated artificial sequence 43-12b VL
source                  1..107
                        mol_type = protein
                        organism = synthetic construct
SEQUENCE: 34
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ TYSGPWTFGQ GTKVEIK               107
```